(12) United States Patent
Smith et al.

(10) Patent No.: US 12,194,276 B2
(45) Date of Patent: Jan. 14, 2025

(54) REMOTELY ACTIVATED CANNULA INSERTION

(71) Applicant: MEDTRONIC MINIMED, INC., Northridge, CA (US)

(72) Inventors: Roger E. Smith, Ivins, UT (US); Matthew William Yavorsky, Granada Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 567 days.

(21) Appl. No.: 17/454,600

(22) Filed: Nov. 11, 2021

(65) Prior Publication Data

US 2022/0143305 A1    May 12, 2022

Related U.S. Application Data

(60) Provisional application No. 63/112,578, filed on Nov. 11, 2020.

(51) Int. Cl.
*A61M 5/142* (2006.01)
*A61M 5/145* (2006.01)
*G16H 20/17* (2018.01)

(52) U.S. Cl.
CPC ...... *A61M 5/14248* (2013.01); *A61M 5/1452* (2013.01); *G16H 20/17* (2018.01); *A61M 2005/14252* (2013.01); *A61M 2005/14506* (2013.01); *A61M 2205/3553* (2013.01)

(58) Field of Classification Search
CPC .............. A61M 5/14248; A61M 2005/14252
See application file for complete search history.

(56) References Cited

U.S. PATENT DOCUMENTS

| | | | |
|---|---|---|---|
| 11,260,171 B2 | 3/2022 | Smith | |
| 2010/0152674 A1* | 6/2010 | Kavazov | A61M 5/1413 604/218 |
| 2019/0015585 A1 | 1/2019 | Smith | |
| 2023/0270933 A1* | 8/2023 | Sjölund | A61M 5/14248 604/131 |

FOREIGN PATENT DOCUMENTS

| | | | | |
|---|---|---|---|---|
| EP | 2818191 A1 | | 12/2014 | |
| EP | 3260151 A1 | * | 12/2017 | |
| EP | 3603700 A1 | * | 2/2020 | ........ A61M 5/14248 |

OTHER PUBLICATIONS

International Search Report and Written Opinion mailed Mar. 9, 2022; International Application No. PCT/US2021/072365; 17 pages.

* cited by examiner

*Primary Examiner* — Laura A Bouchelle
(74) *Attorney, Agent, or Firm* — Fortem IP LLP

(57) ABSTRACT

Infusion devices are disclosed herein. The present technology includes, for example, an infusion device for delivering a medicament to a body of a user. The device can comprise an insertion assembly comprising a cannula, a reservoir assembly comprising a reservoir configured to receive a medicament, and a trigger assembly configured to trigger insertion of the cannula into the user in response to a command from a remote computing device communicatively coupled to the infusion device.

19 Claims, 21 Drawing Sheets

REMOTELY ACTIVATED CANNULA INSERTION

CROSS-REFERENCE TO RELATED APPLICATION

This application claims the benefit of priority to U.S. Provisional Application No. 63/112,578, filed Nov. 11, 2020, which is incorporated by reference herein in its entirety.

TECHNICAL FIELD

The present technology relates generally to medical devices, and more particularly, to remotely activated cannula insertion.

BACKGROUND

Ambulatory infusion pumps are relatively small, at least substantially self-contained devices that are used to introduce drugs and other infusible substances (collectively "medicament") into users' bodies. Some infusion pumps are configured to be worn on a belt, carried in a clothing pocket, or the like. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin. Other exemplary medicaments that may be introduced by an infusion pump include, but are not limited to, drugs that treat cancers and drugs that suppress the perception of pain.

Many conventional infusion pumps have improved user health and quality of life. Nevertheless, the present inventors have determined that conventional infusion pumps are susceptible to a wide range of improvements. By way of example, but not limitation, the present inventors have determined that it would be desirable to provide an infusion pump that is smaller, simpler, more reliable, and less costly than conventional infusion pumps, while also being more accurate and user-friendly than conventional infusion pumps.

SUMMARY

Several aspects of the present technology include an infusion device for delivering a medicament to a body of a user. The infusion device can include, for example, an insertion assembly comprising a cannula, a reservoir assembly comprising a reservoir configured to receive a medicament, and a motor configured to rotate in a first direction to cause the medicament to flow out of the reservoir to the cannula, and in a second, reverse direction to trigger insertion of the cannula into the user in response to a command from a remote computing device communicatively coupled to the infusion device.

In some embodiments, the insertion assembly includes a cannula carrier and the cannula is fixed to the cannula carrier. The cannula carrier can be configured to rotate from a first position in which the cannula carrier is locked in a pre-insertion state to a second position in which the cannula carrier is free to move to insert the cannula. In several of such embodiments, the cannula carrier is rotationally biased towards the second position.

According to several embodiments, the infusion device includes a trigger assembly moveable between a first configuration in which the trigger assembly opposes motion by the cannula carrier towards the second position, and a second configuration in which the trigger assembly allows motion of the cannula carrier towards the second position. In several of such embodiments, movement of the motor in the second, reverse direction causes the trigger assembly to move from the first configuration to the second configuration, thereby permitting movement of the cannula carrier for cannula insertion. The trigger assembly can comprise a ratchet that permits movement of the cannula carrier when the motor rotates in the second, reverse direction. In some embodiments, the trigger assembly comprises a hydraulic cylinder.

Some aspects of the present technology include a trigger assembly configured to move out of engagement with the cannula carrier when the motor rotates in the second, reverse direction.

The infusion device of claim 2, further comprising a trigger assembly configured to push the cannula carrier into the second position when the motor rotates in the second, reverse direction.

The infusion device of claim 2, further comprising a trigger assembly configured to pull the cannula carrier into the second position when the motor rotates in the second, reverse direction.

The present technology includes methods for operating an infusion device. A method can include, for example, rotating a motor of an infusion device in a first direction to determine a volume of medicament in a reservoir of the infusion device; receiving a command from a remote controller to rotate the motor in a second direction opposite the first direction; and rotating the motor in the second direction, thereby triggering insertion of a cannula of the infusion device. In some embodiments, the method further comprises rotating the motor in the first direction, after rotating the motor in the second direction, to deliver the medicament through the cannula.

According to several methods, the infusion device comprises a cannula carrier and the cannula is fixed to the cannula carrier. The cannula carrier can be configured to rotate from a first position in which the cannula carrier is locked in a pre-insertion state to a second position in which the cannula carrier is free to move to insert the cannula. Rotation of the motor in the second direction can cause the cannula carrier to move from the first position to the second position. In some embodiments, rotation of the motor in the second direction causes a trigger assembly to push the cannula carrier from the first position into the second position. In other embodiments, rotation of the motor in the second direction causes a trigger assembly to pull the cannula carrier from the first position into the second position.

In some aspects of the present technology, the cannula carrier is biased towards rotating towards the second position. For example, rotation of the motor in the second direction can cause disengagement of a trigger assembly with the cannula carrier, thereby allowing the cannula carrier to rotate into the second position. In some embodiments, rotating the motor in the second direction causes simultaneous rotation of a ratchet wheel in the second direction. In several embodiments, rotating the motor in the second direction activates a linear clutch coupled to a reservoir assembly of the infusion device.

According to some embodiments, the infusion device comprises an insertion assembly comprising a cannula, a reservoir assembly comprising a reservoir configured to receive a medicament, and a trigger assembly coupled to the insertion assembly and in fluid communication with the reservoir. In response to a command from a remote computing device communicatively coupled to the infusion device, the reservoir assembly can deliver medicament to the trigger assembly to trigger insertion of the cannula by the insertion assembly. The infusion device can comprise a motor that is actuated by the command from the remote computing device and, when actuated, causes delivery of medicament from the reservoir to the trigger assembly. In some embodiments, the reservoir includes a pusher and the infusion device further comprises a motor that is actuated by the command from the remote computing device. When actuated, the motor advances the pusher within the reservoir to cause delivery of medicament from the reservoir to the trigger assembly. In several embodiments, delivery of medicament to the trigger assembly to trigger insertion of the cannula does not cause infusion of the medicament into the patient. The trigger assembly can be configured to engage the insertion assembly to prevent cannula insertion, and wherein medicament delivered into the trigger assembly causes the trigger assembly to disengage the insertion assembly, thereby allowing the insertion assembly to insert the cannula.

According to several embodiments, the infusion device comprises an insertion assembly comprising a cannula carrier and the cannula is fixed to the cannula carrier. The cannula carrier can be configured to rotate from a first position in which the cannula carrier is locked in a pre-insertion state to a second position in which the cannula carrier is free to move to insert the cannula. In some embodiments, the trigger assembly is mechanically coupled to the cannular carrier and prevents the cannula carrier from rotating towards the second position.

In some embodiments, the trigger assembly comprises a tubular housing defining a lumen therein and a piston positioned within the lumen, and wherein the lumen is in fluid communication with the reservoir. Delivery of medicament to the trigger assembly to trigger insertion of the cannula can move the piston, and movement of the piston by a predetermined amount aligns a portion of the piston with a portion of the insertion assembly to trigger cannula insertion. In some embodiments, the trigger assembly comprises a hydraulic slave cylinder.

Some methods for operating an infusion device comprise receiving a command from a remote computing device to actuate a motor of the infusion device, where the infusion device having a reservoir containing a medicament, an insertion assembly comprising a cannula, and a trigger assembly coupled to the insertion assembly and in fluid communication with the reservoir. In response to the command, actuating the motor to push at least some of the medicament stored within the reservoir into the trigger assembly, thereby causing the insertion assembly to drive the cannula out of the infusion device.

Some methods for operating an infusion device comprise receiving a command from a remote computing device to rotate a motor of the infusion device in a first direction, thereby causing an insertion assembly of the infusion device to drive a cannula out of the infusion device. After rotating the motor in the first direction, rotating the motor in a second direction opposite the first direction to push a medicament stored in a reservoir of the infusion device through the cannula.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology comprises infusion devices configured to be adhered to the user's skin above the delivery site (sometimes referred to as "patch pumps"). The infusion devices include a reservoir configured to receive and contain a medicament, a motor, and an insertion assembly having a cannula that is to be operatively connected to the reservoir. After applying the device to the skin, the user activates the insertion assembly to insert the cannula subcutaneously. Often times this insertion step requires the user to manually press or pull a trigger on the device, which can be burdensome for the patient. Disclosed herein are infusion devices configured for remotely triggered cannula insertion (e.g., triggered by a computing device that is separate from but communicatively coupled to an infusion device). As described in greater detail below, the infusion devices herein are configured to be communicatively coupled to a remote controller that, at the user's command, sends instructions to the infusion device that causes the insertion assembly to deploy the cannula. In some embodiments, the instructions cause a predetermined rotation of the motor, and the infusion device includes a trigger assembly that leverages the motor's rotations to move or allow movement of the insertion assembly to a cannula-release position. In any case, the infusion devices of the present technology enable cannula insertion via remote control, which can be more convenient for the user than conventional manual triggers.

Figure 1A:
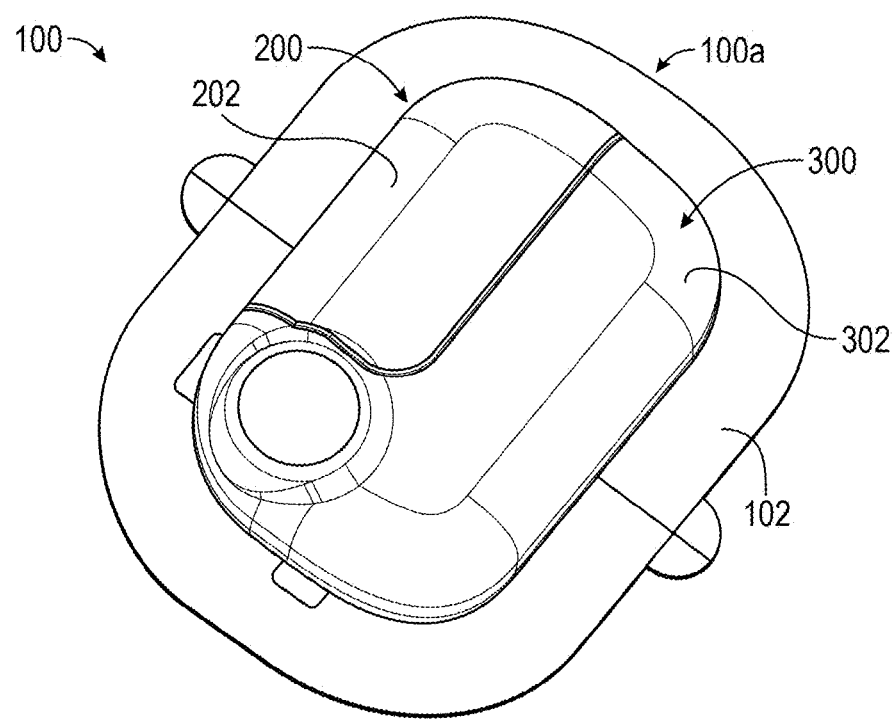
FIG. 1A is a perspective view of an infusion device in accordance with several embodiments of the present technology.
Figure 1B:
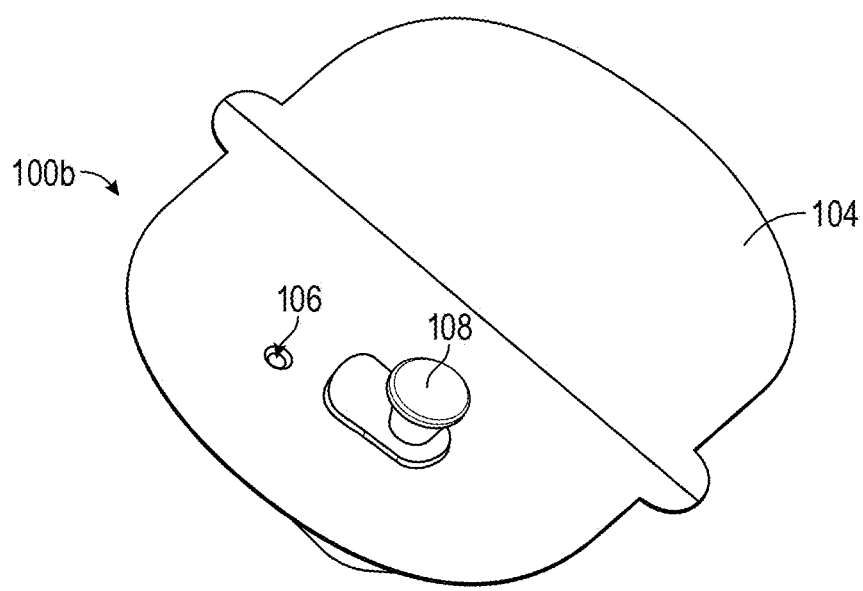
FIG. 1B is a perspective view of the bottom of the infusion device of FIG. 1A.

FIGS. 1A and 1B show top and bottom sides, respectively, of an infusion device 100 in accordance with several embodiments of the present technology. As previously mentioned, the bottom side 100b of the device 100 is configured to be adhered to the user's skin with the top side 100a facing away from the user. The device 100 includes a durable assembly 200 and a disposable assembly 300, each having respective housings 202 and 302. The durable assembly 200 and disposable assembly 300 are disposed on an adhesive pad 102 with adhesive backing 104 for securing to the user's skin. The bottom side 100b of the device 100 may also include a pull-before-use plug (PBUP) 108 and a fill port 106.

The device 100 may be used in conjunction with a wide variety of remote controllers. The remote controller, for example, can be a device-specific controller, a mobile phone, a tablet, etc. Such remote controllers may be used, for example, to allow the user to transmit instructions to the durable assembly 200 or otherwise facilitate communication between durable assembly 200 and the user (e.g., an alarm condition message or other message concerning the conditions of device 100). In some embodiments, the remote controller is configured to send instructions to and/or receive instructions from the disposable assembly 300.

The remote controller may be configured to facilitate one, some, or all of the following operations:
- turning the remote controller on or off;
- associating (or "assigning") the remote controller to the durable assembly 200;
- obtaining status information such as medicament level, battery charge level, and/or alarm conditions;
- silencing the durable assembly's alarm;
- selecting options that may be associated with the durable assembly's alarm such as type of alarm (audible, palpable, visible or combinations thereof) and strength/volume of alarm;
- connecting the remote controller to a computer to, for example, update the remote controller or durable assembly firmware, load and delete delivery profiles stored in the durable assembly 200 or remote controller, and otherwise reprogram the durable assembly 200 and/or the remote controller;
- selecting medicament options such as medicament concentrations;
- selecting a stored medicament delivery profile;
- increasing and decreasing medicament dose rate;
- triggering cannula insertion;
- initiating medicament delivery;
- pausing a dispensing operation;
- and/or other processes.

A user may pause delivery in order to remove or replace a user-applied structure (e.g., a disposable assembly), adjust for a current or anticipated changed body condition (e.g., low glucose, vigorous exercise), follow a physician's suggestion, or disconnect the durable assembly 200 from the body for any other reason.

In some embodiments, the remote controller is configured to generate an indicator, based on information from a microprocessor of the durable assembly 200, that is indicative of, for instance, the amount of time remaining in the current dispensing program, the amount of time until the next disposable assembly replacement, etc. The indicator may be audible, visible, palpable or combinations thereof. A time remaining indicator may be useful for a variety of reasons. For example, knowledge of the time remaining before the next disposable assembly replacement allows the user to determine, based at least in part on the current time of day and upcoming events (e.g., travel or sleep), whether or not it would be more convenient to replace the disposable assembly 300 at a time before the end of the dispensing program. Additionally or alternatively, the remote controller can also be configured to generate an indicator for the amount of insulin remaining and/or an indicator for the battery power.

With respect to dimensions, the device 100 can have a length of about 35-60 mm; a width of about 30-45 mm; and an overall thickness or height of about 8-18 mm. Suitable housing materials include, but are not limited to, plastic or other materials having a modulus of elasticity of 0.2-1.0 million psi.

To use the infusion device 100, the user (e.g., the patient) connects the disposable assembly 300 to the durable assembly 200. Unless the reservoir of the disposable assembly 300 has been sufficiently pre-loaded, the user injects a desired amount of medicament into the reservoir via the fill port 106. A plunger seek procedure (detailed below) may be initiated, either by the user or automatically. To adhere the device 100 to the user, the adhesive backing 104 may be peeled off to expose the adhesive pad 102; the PBUP 108 may be removed; and/or the device 100 may be positioned over the chosen body location and pressed gently to adhere the adhesive pad 102 to the skin surface. In some embodiments, the user triggers the automatic cannula insertion via the remote controller (e.g., after the plunger seek operation is complete). In some embodiments, plunger seek is not required.

Figure 2A:
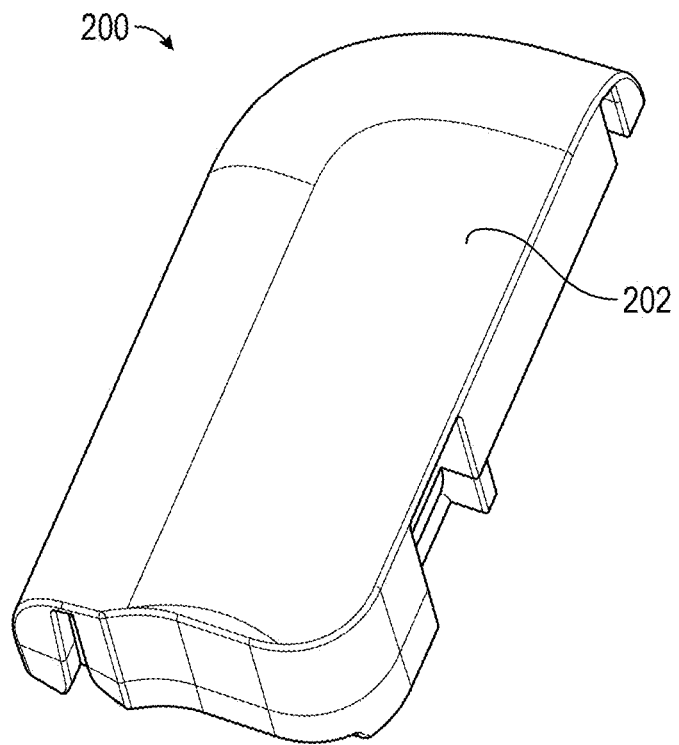
FIG. 2A is a perspective view of a durable assembly of the infusion device of FIGS. 1A and 1B.
Figure 2B:
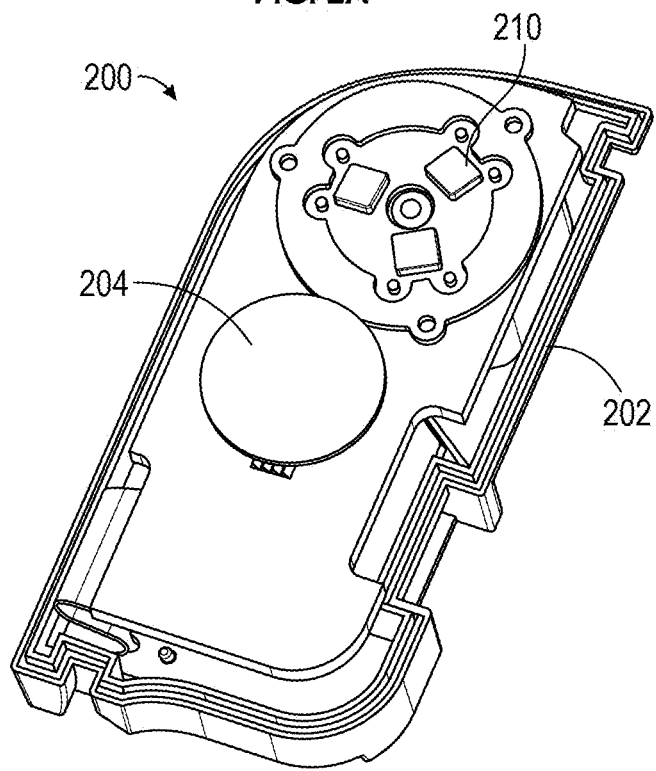
FIGS. 2B and 2C are perspective views of certain components of the durable assembly illustrated in FIG. 2A.
Figure 2C:
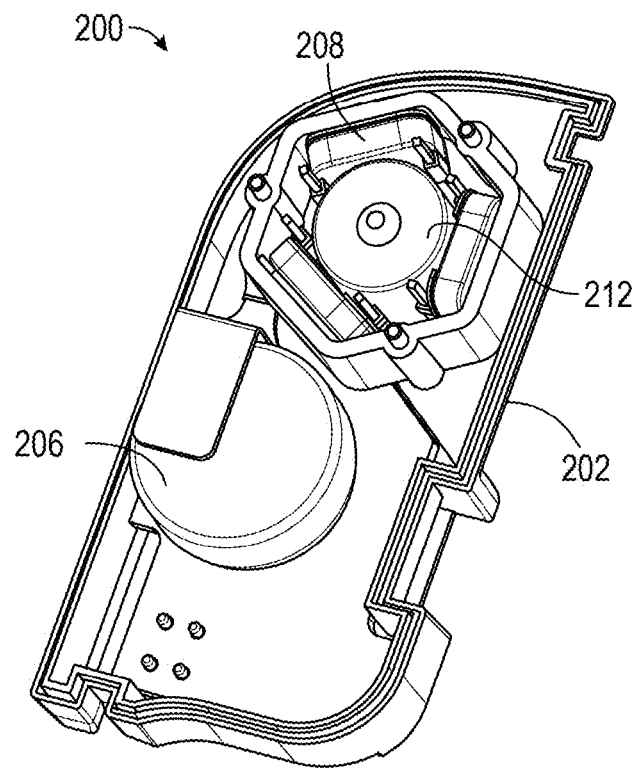

The durable assembly 200, shown in more detail in FIGS. 2A-2C, may include a housing 202, a buzzer or other alarm device 204, one or more batteries or other energy supply 206, a microprocessor (not shown), and a coil assembly 208 (which functions as a motor stator) including one or more Hall-effect sensors 210. In some embodiments, the energy supply 206 is a rechargeable battery, such as a rechargeable lithium battery, with enough power to drive the motor continuously without needing a capacitor or other additional energy storage device.

Figure 3A:
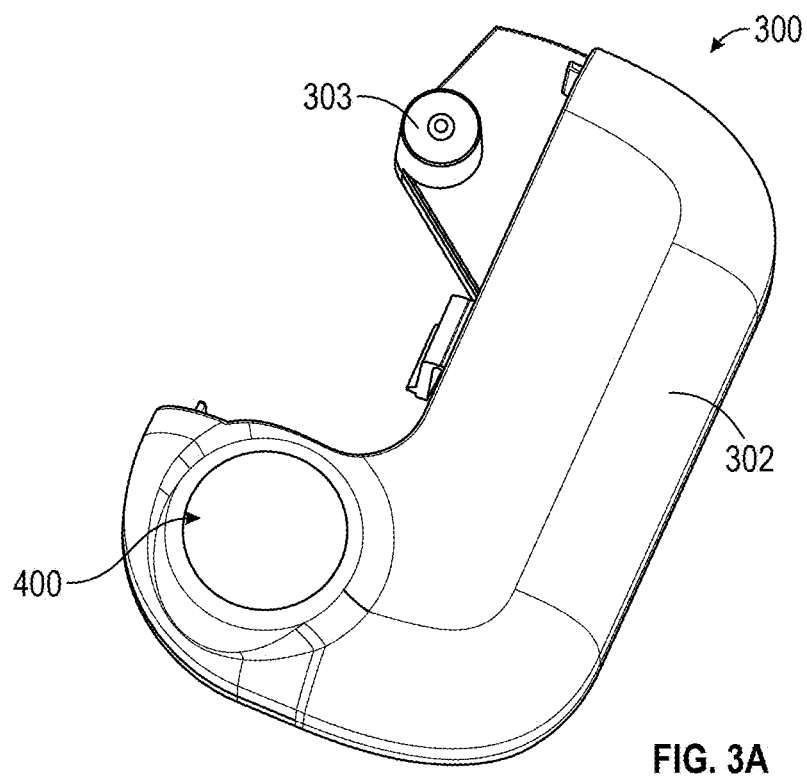
FIG. 3A is a perspective view of a disposable assembly of the infusion device of FIGS. 1A and 1B.
Figure 3B:
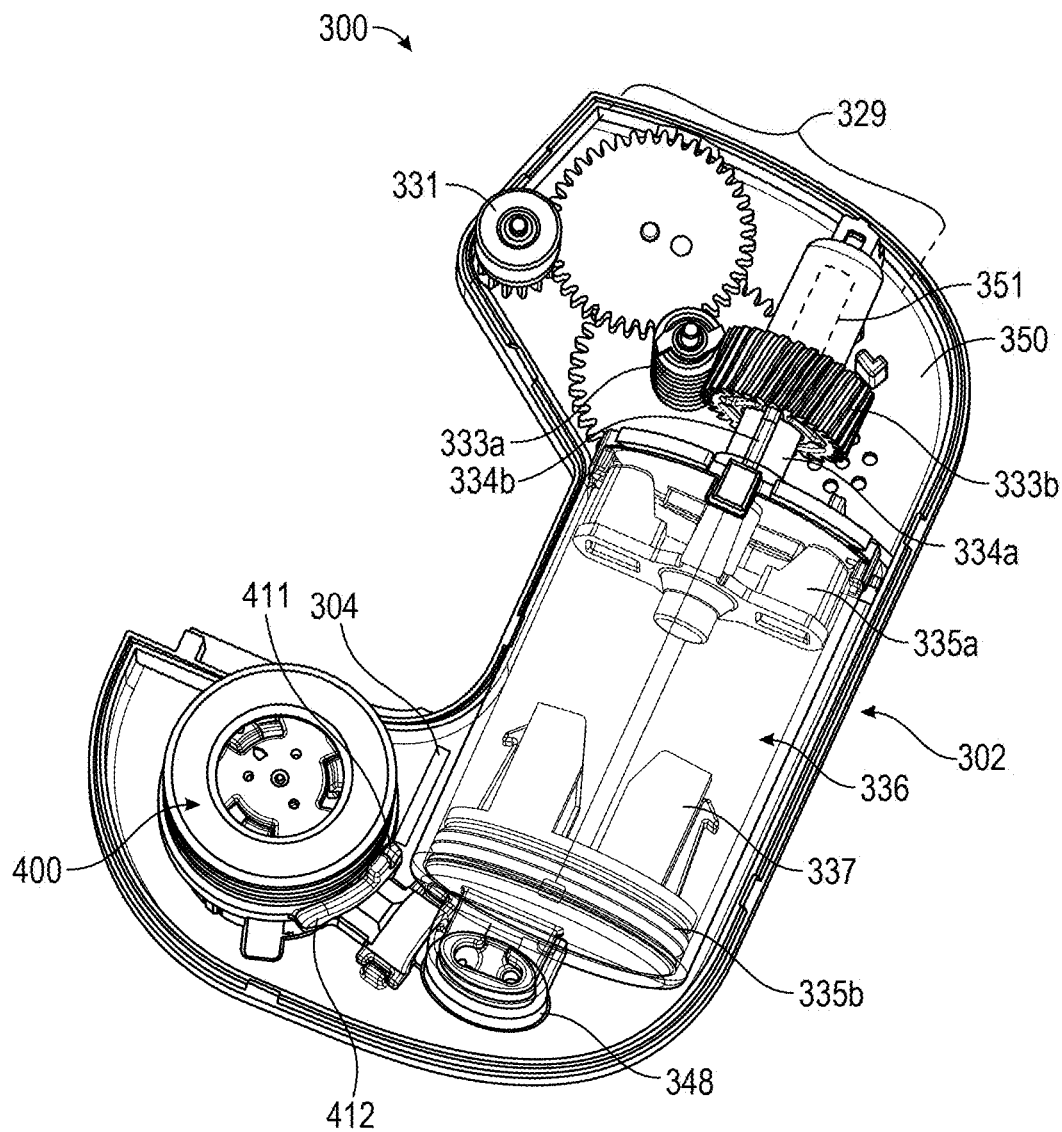
FIG. 3B is a perspective view of certain components of the disposable assembly illustrated in FIG. 3A.

Referring specifically to FIG. 2C, the coil assembly 208 can be positioned around a recessed portion 212 of the durable assembly housing 202 that is configured to fit over a protruding portion 303 of the disposable housing 302 (FIG. 3A), which in turn fits over a magnetic motor rotor 331 of the disposable assembly 300 (FIG. 3B). In this two-piece motor, the motor's coil assembly 208 is in the durable assembly 200 and is positioned around the motor rotor 331 that is part of the disposable assembly 300. The Hall-effect sensors 210 are positioned above the coil assembly 208 in the durable assembly 200. In this configuration, there is a gap between the motor coil assembly 208 and the motor rotor 331. Some or all of the gap may be defined by (and occupied by) housing portions, e.g., durable housing portion 212 and disposable housing portion 303 in the illustrated implementation. In other implementations, the gap between the motor coil assembly 208 and the motor rotor 331 may be occupied by only a portion of the durable assembly housing 202, or only a portion of the disposably assembly housing 302, or no structure at all and may simply be an air gap. The size of the gap, which is defined by the distance between the motor coil assembly 208 and the motor rotor 331, is typically about 0.5 mm to 2.0 mm. As such, there is no gear engagement or other mechanical connection between the durable assembly 200 and the disposable assembly 300. All electronics may be positioned within the durable assembly 200, with the energy needed by the disposable assembly 300 transferred by electromagnetic torque coupling, which is a coupling without direct mechanical coupling or electrical contact from the durable assembly 200. These designs afford the additional advantage of being relatively simple to make waterproof, or at least water resistant.

An exemplary motor rotor 331 may be a 2-pole, cylinder-shaped, rare earth (such as neodymium) rotor, magnetized across the diameter, with a 5 mm diameter and 5 mm height. Other suitable motor rotors may be larger or smaller, or be multi-pole. Motor rotors of this type typically cost about 5 cents per piece, helping control the total cost of disposable assembly 300. The microprocessor (not shown) directs rotation of motor rotor 331 by sequentially energizing the coils of motor coil assembly 208 to create an electromagnetic torque coupling between the motor coil assembly 208 and the motor rotor 331. The position/orientation of the rotor's poles relative to the rotating magnetic field generator (coil assembly 208) is measured by back EMF, a rotary encoder (s), one or more Hall-effect sensors 210, or the like. For instance, the Hall-effect sensors 210 mounted above the coil windings 208 may be used to supply the microprocessor a count, a tachometer signal, or rotor position, allowing low-cost, closed-loop control of the rotor speed. Brushless motors of this type are efficient and run very cool.

The disposable assembly 300, shown in more detail in FIGS. 3A and 3B, may include a reservoir assembly, a trigger assembly 304 (shown schematically), and an insertion assembly 400, all mounted on a baseplate 350. The reservoir assembly can comprise a drive assembly 329, a reservoir 336, a plunger pusher 335a, and a plunger 335b. The plunger pusher 335a is coupled to the drive assembly 329, and both the plunger pusher 335a and the plunger 335b are contained within the reservoir 336. The insertion assembly 400 includes a cannula 441 (see FIG. 4A) and several components for driving the cannula 441 into the user's skin. The trigger assembly 304 can operatively couple one or more components of the reservoir assembly to the insertion assembly 400 to control the timing of insertion of the cannula 441. In some embodiments, for example, one or more components of the trigger assembly 304 are operatively coupled to the gear train 332 such that remote activation of the motor moves the trigger assembly 304 into or out of engagement with the insertion assembly 400, thereby actuating the insertion assembly 400 and releasing the cannula. Additional details regarding remotely-actuatable trigger assemblies are discussed below with reference to FIGS. 8-12B.

Referring still to FIGS. 3A and 3B, the drive assembly can comprise the magnetic motor rotor 331 and a gear train 332. The gear train 332 is attached to the pusher 335a which is positioned in the reservoir 336. The magnetic motor rotor 331 may be mechanically attached through the gear train 332 to affect translation of the plunger pusher 335a (and the plunger 335b, when attached to the plunger pusher 335a) within the reservoir 336.

As best seen in FIG. 3B, the gear train 332 includes a worm drive comprised of a worm screw 333a and a worm gear 333b, and also a lead screw nut 334a and a fine-pitch lead screw 351 (enclosed by the lead screw nut 334a). The worm gear 333b is coupled to the lead screw 351 via the lead screw nut 334a. Protrusions 334b on the lead screw nut 334a correspond with recesses (not shown) inside the worm gear 333b, and a threaded portion (not shown) inside the lead screw nut 334a pairs with the thread on the lead screw 351 enclosed by the lead screw nut 334a. The configuration of the gear train 332 prevents back-driving due to reservoir pressure, eliminating the need for a clutch or other locking mechanism. Suitable materials for the components of the gear train 332 include, but are not limited to, stainless steel or high strength plastic, such as nylon, acetal (Delrin.RTM.) or polycarbonate.

The reservoir 336 may be prefilled with a medicament. The medicament, for example, can be U-100 insulin or U-500 insulin or other concentrations of insulin to suit different user use profiles, or may be user-fillable by way of the fill port 106 (FIG. 1B). In some embodiments, the reservoir 336 can be mounted on a reservoir support block (not shown in FIG. 3B). A reservoir outlet fitting 348 is in fluid communication with the reservoir 336. The reservoir outlet fitting 348 can be made from a drug-compatible material, such as, but not limited to, polypropylene, cyclic olefin polymer (COP) or polyethylene.

In those cases where the reservoir 336 is filled by the user, the user may completely fill the reservoir to capacity with medicament, or the user may choose to introduce less medicament and not completely fill the reservoir. Since an unknown amount of medicament may be injected into a user-filled reservoir, a plunger-pusher zeroing procedure (or "plunger seek") may be user-initiated or may be an automatic aspect of pump operation. A plunger seek procedure precisely determines and/or sets, before any medicament dispensing, exactly how far the plunger pusher 335a travels before it engages the plunger 335b, allowing a calculation to determine the amount of medicament in the reservoir and, therefore, an estimate of time-to-empty and time for disposable assembly replacement.

FIG. 3B shows the reservoir 336 before any medicament is introduced into the reservoir 336. The plunger 335b is disconnected from the plunger pusher 335a (and thus free-floating) and the plunger pusher 335a is in the fully-retracted position. At this point, and until the plunger seek operation is complete, the PBUP 108 (FIG. 1B) remains in place to prevent premature flow of medicament between the reservoir 336 and the insertion assembly 400 (except in the hydraulic trigger embodiments discussed below with reference to 11A-12B, in which a PBUP may not be necessary). As medicament is introduced into the reservoir 336 via the fill port 106, the plunger 335b is pushed towards the plunger pusher 335a. If the reservoir 336 is filled to capacity, the plunger 336b will be pushed into contact with the plunger pusher 335a. In some embodiments, this causes the hooks 337 (or other suitable method of attachment) on the plunger 335b to engage with and permanently lock with the pusher 335a. If the reservoir 336 is not filled to capacity, the plunger 335b will be positioned at some unknown point within the reservoir 336 until the plunger seek operation is complete. Once the user has introduced medicament into the reservoir 336, a plunger seek operation can be initiated by the user or may be an automatic aspect of pump operation. When the plunger seek operation is initiated, the motor advances the plunger pusher 335a until it contacts the plunger 335b. In some embodiments, they lock together with plunger hooks 337 or some other suitable method of attachment. In some embodiments, the plunger pusher 335a and the plunger 335b are not configured to mechanically lock. The reservoir 336 and the plunger 335b may be made of cyclic olefin polymer (COP), polypropylene or other drug-compatible polymeric material. Suitable materials for the plunger pusher 335a include, but are not limited to, stainless steel, COP, nylon, and polycarbon.

As previously mentioned, the plunger seek operation is performed when flow from the reservoir 336 is blocked by the PBUP 108. Given there may be tolerances associated with cartridge manufacture and variation in medicament filling, there may be variations in the distance that the plunger pusher 335a travels from its initial home position before it contacts the plunger 335b. Under microprocessor control, the motor advances the plunger pusher 335a into contact with the plunger 335b, causing increased fluid path pressure. The Hall-effect sensors 210, an encoder, or other monitoring/sensing device is sampled to determine when a motor stall occurs as the plunger pusher 335a is advanced. Lack of signals from the Hall-effect sensors 210 indicates that the motor is not turning. The motor stall is presumed to be due to hydraulic lock and, therefore, indicative of the plunger pusher 335a contacting the plunger 335b of a plugged device. In some embodiments, the procedure may employ two or more speeds for advancing the plunger pusher 335a. Also, the plunger pusher 335a may be advanced at a controlled torque, or limited force, so that the motor will stall with the least amount of force possible for reliable results, in order to reduce the load on the system (e.g., the bearings and the battery). As stated above, knowing the distance the plunger pusher 335a traveled before contacting the plunger 335b allows calculations of medicament volume and estimated time until replacement of the disposable assembly 300.

In some embodiments, instead of or in addition to sensing motor stall (as described above), the device 100 can be configured to sense an increased load on the motor. For instance, the device 100 can be configured to sense a motor speed reduction that is less than 100% (which would be equivalent to a motor stall), which could be sensed sooner than a motor stall. The device 100 can be configured to sense, for example, a 10%, 20%, 30%, 40%, 50%, 60%, 70%, 80% or 90% in speed reduction. Suppose, for example, the device 100 is running the motor in a speed-controlled manner by varying the motor current to control the speed. When the reservoir pressure increases, the motor current is increased to maintain a desired speed. Accordingly, the device 100 is configured to sense occlusion and plunger seek by sensing increases in motor load. This increased load can be sensed by a number of ways such as power increase, speed decrease, etc.

Figure 4A:
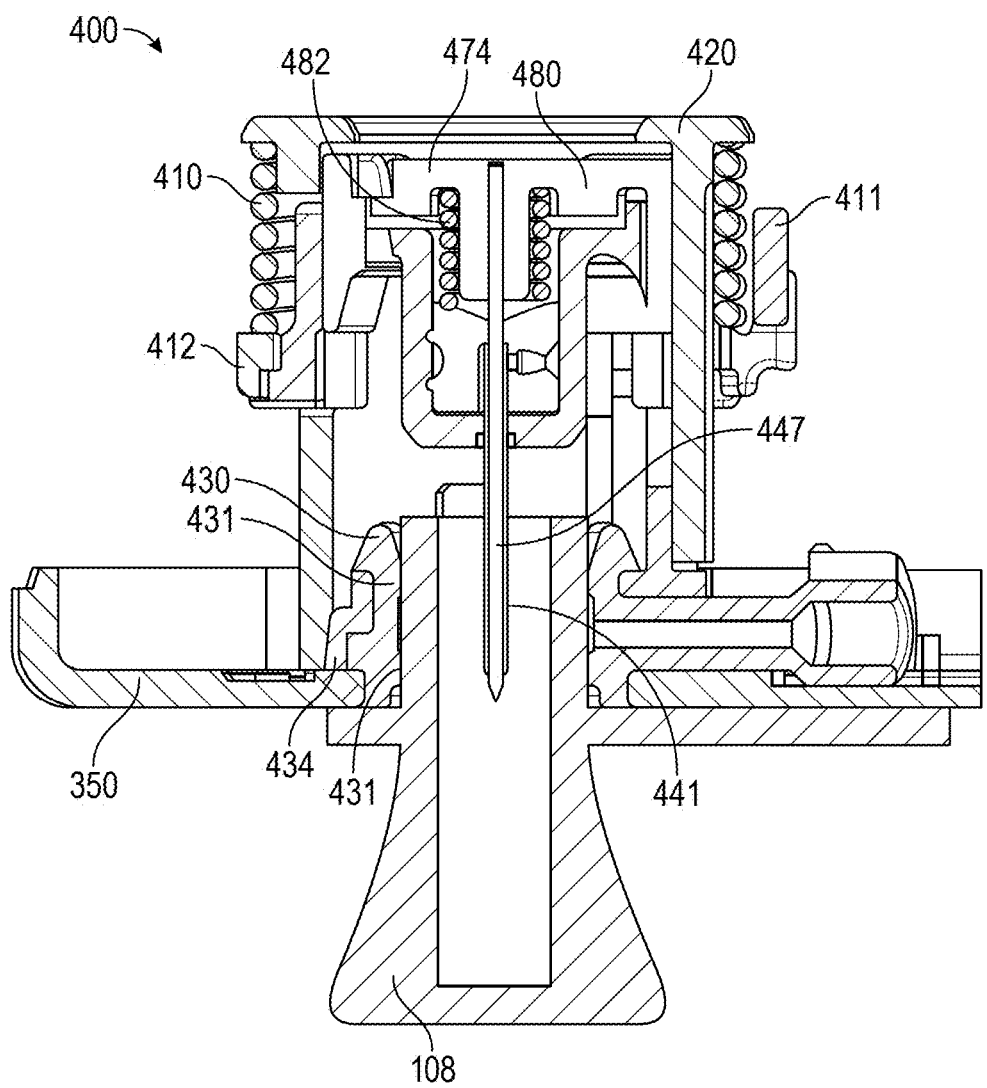
FIG. 4A is a section view showing an insertion assembly of the disposable assembly illustrated in FIG. 3A, shown in state one.
Figure 4B:
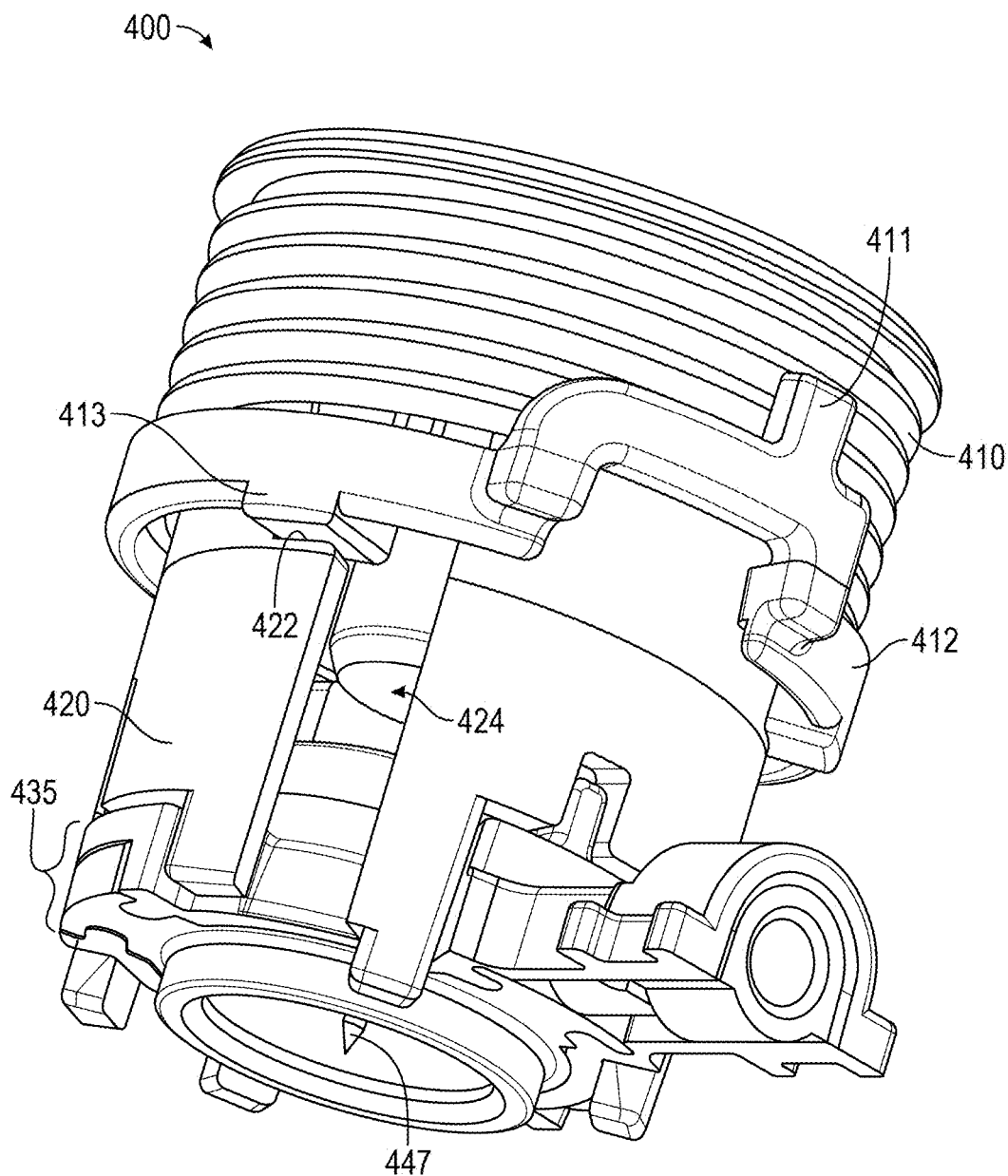
FIG. 4B is a perspective view of the insertion assembly shown in FIG. 4A.

The insertion assembly 400 is shown in greater detail in FIGS. 4A and 4B. FIGS. 4A and 4B show the insertion assembly 400 in a cocked and locked position (e.g., before the user removes the PBUP 108 and remotely activates the trigger assembly 304). The insertion assembly 400 can comprise a cylindrical guide housing 420, a main insertion spring 410, a cannula carrier 412, and a cannula 441 fixed to the cannula carrier 412. The cannula carrier 412 further includes a trigger boss 411 that is configured to engage with the trigger assembly 304 to move (or allow movement of) the cannula carrier 412. The main insertion spring 410 extends between a top ledge of the guide housing 420 and a portion of the cannula carrier 412. When the insertion assembly 400 is in a pre-insertion position (shown in FIG. 4A), the main insertion spring 410 is in a compressed state and exerts a downward force on the cannula carrier 412. Engagement between the cannula carrier 412 and a support ledge 422 (FIG. 4B) of the guide housing 420 holds the main insertion spring 410 in a compressed state and prevents downward motion of the cannula carrier 412.

The insertion assembly 400 also includes a trocar 447, a trocar carrier 474, a trocar seal 480, a trocar retraction spring 482, a cannula seal 430, seal rings 431, and a cannula seal retainer 434. The trocar 447, which comprises an elongate rod with a sharp distal tip, may be made of metal, such as stainless steel, or other relatively rigid biocompatible material, such as rigid plastic, ceramic, or other rigid biocompatible material, and is used to penetrate the skin and a short distance into the flesh, to make a channel for cannula 441. The cannula 441 may be made of polytetrafluoroethylene (PTFE), such as TEFLON.RTM. PTFE, or other biocompatible polymeric material. As described further below, these components provide a highly efficient cannula seal with low cannula insertion forces and a highly reliable medicament seal. The components involved and details of how the insertion assembly 400 performs these actions are described in more detail below.

The insertion assembly 400 may be a 4-state system. FIGS. 4A-4B show the insertion assembly 400 in its first state: the cocked position (e.g., before the user removes the PBUP 108 and remotely activates the trigger assembly 304 to insert the cannula 441). In this state, the PBUP 108 is positioned to occlude the fluid path from the reservoir 336 and the cannula carrier 412 is held up above and spaced apart from the cannula seal 430, as described further below. In this state, and as best seen in FIG. 3B, the plunger seek procedure described above can advance the plunger pusher 335a into contact with the plunger 335b, slightly pressurizing the reservoir 336, without injecting medicament into the user. As best seen in FIG. 4A, a seal is formed between the seal rings 431 and the outer surface of PBUP 108, allowing the pressures for plunger seek.

FIGS. 5A-5D show the insertion assembly 400 in its second state. In this state, the PBUP 108 has been removed and the insertion assembly 400 is ready to fire. The fluid path from the reservoir 336 (FIG. 3A) is open to the atmosphere, and any residual pressure is vented before cannula insertion.

As will be described in greater detail below, removal of the PBUP 108 allows cannula insertion, which may be triggered based on activating the trigger assembly 304 via the remote controller. Triggering cannula insertion may cause the trocar 447 and the cannula 441 (best seen in FIG. 5D) to project out of the disposable assembly 300 (that is state three, shown in FIGS. 6A and 6B), and then cause the trocar 447 to retract back into the insertion assembly 400, leaving the cannula 441 in place (which is state four, shown in FIGS. 7A-7D).

Figure 5A:
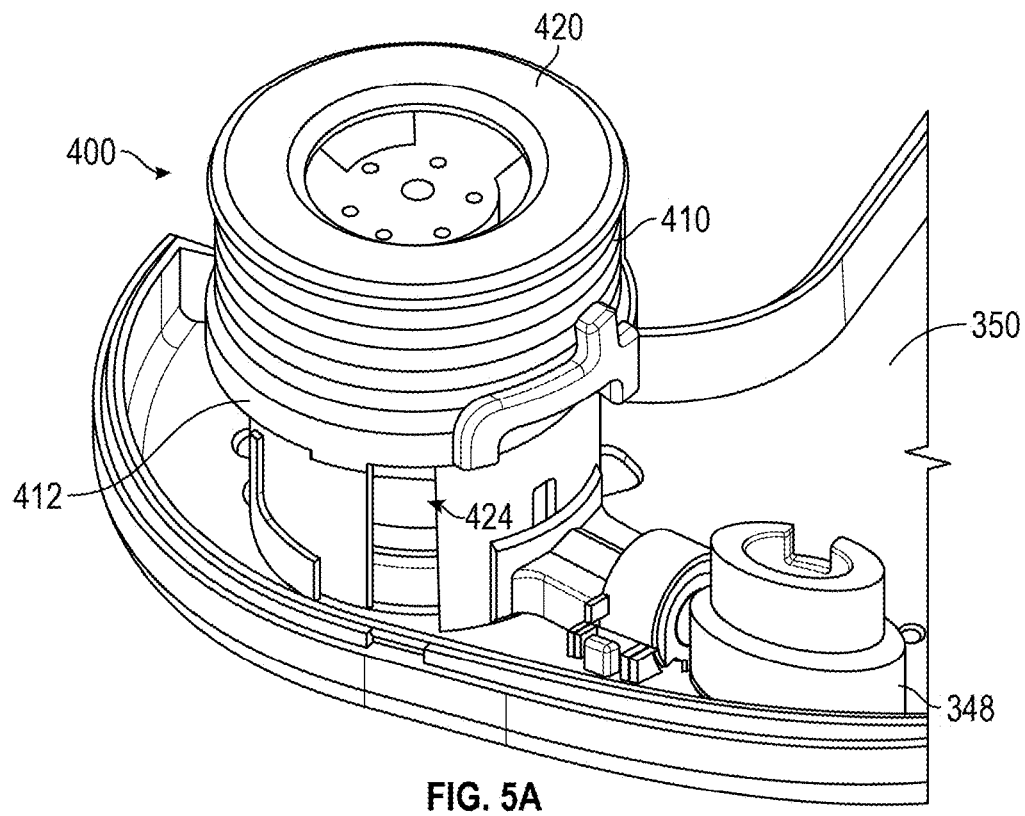
FIGS. 5A and 5B are perspective views of certain components of a disposable assembly, shown in state two, before cannula insertion.
Figure 5B:
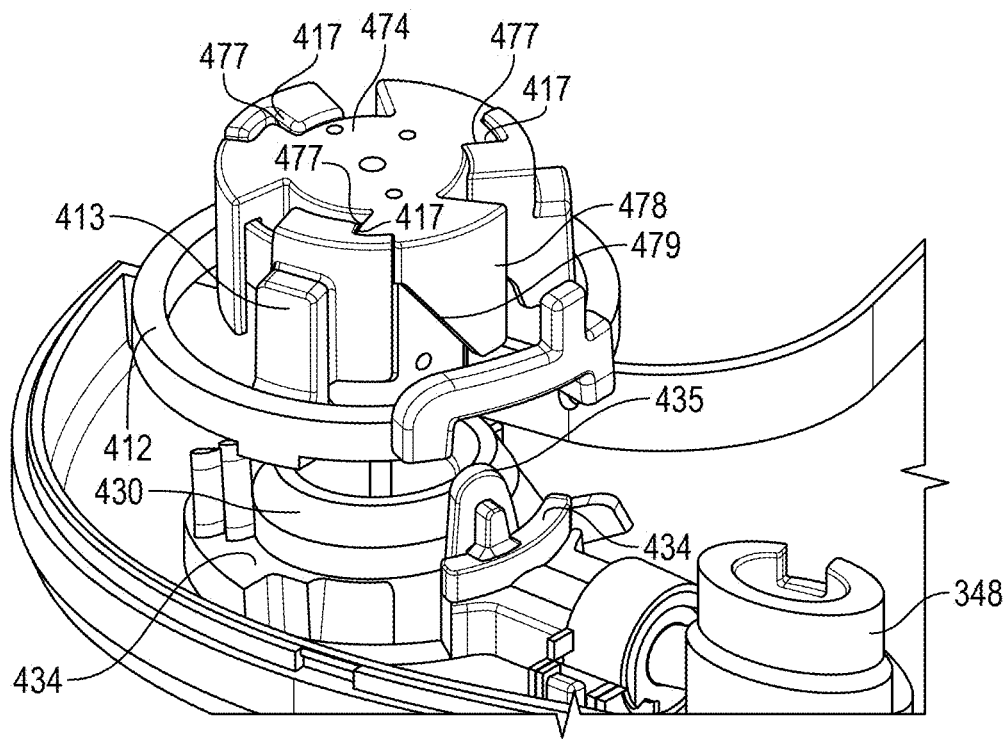
Figure 5C:
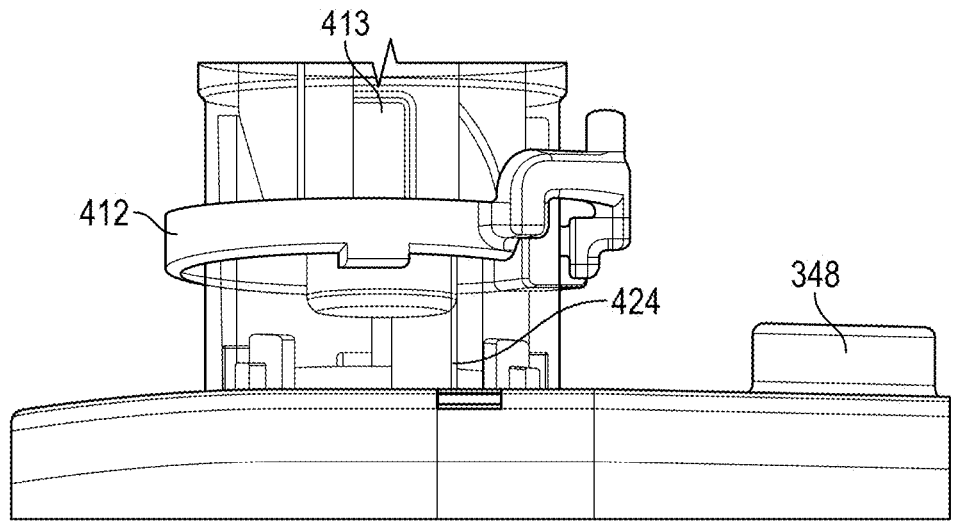
FIG. 5C is a side view showing additional components for use with the components of FIGS. 5A and 5B, shown in position before cannula insertion.
Figure 5D:
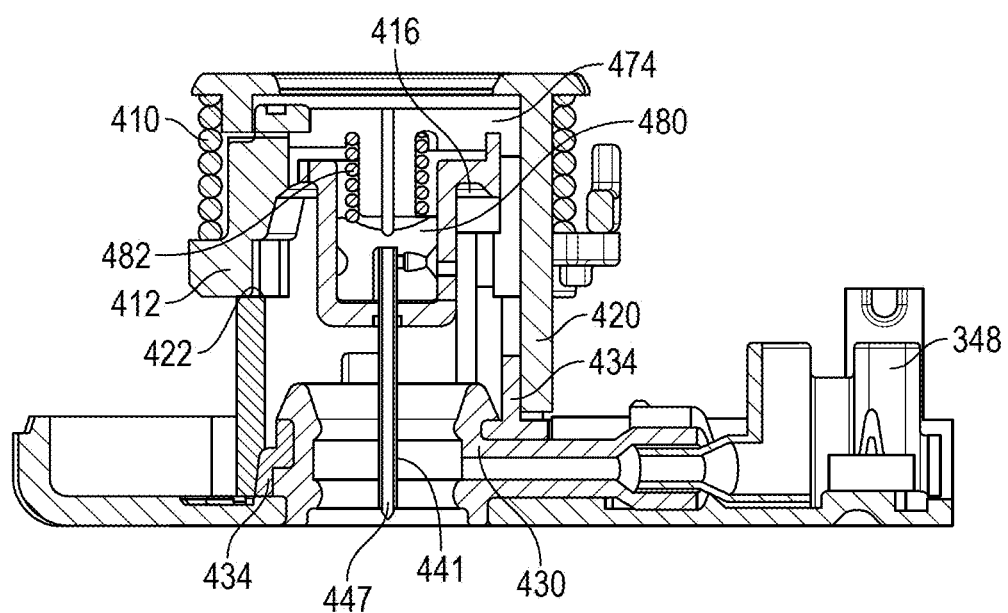
FIG. 5D is a section view showing additional components for use with the components of FIGS. 5A-5C, shown in position before cannula insertion.

FIG. 5B shows the insertion assembly 400 with the main insertion spring 410 and the guide housing 420 removed. In FIG. 5C, the main insertion spring 410 is removed and guide housing 420 is semi-transparent. FIG. 5D is a section view of the components of FIG. 5C. The main insertion spring 410 may provide travel of about 7 mm with a starting force of about 15 newtons (N) and an ending force of about 7 N, and may be made of, for instance, 0.75 mm diameter music wire, with 6 turns and an outside dimension of 13.25 mm. The trocar retraction spring 482 may provide travel of about 7 mm with a starting force of about 4 N and an ending force of about 1 N, and may be made of, for instance, 0.5 mm diameter music wire, with 6 turns and an outside dimension of 3 mm. The guide housing 420 and the cannula seal retainer 434 may be made of high strength plastic, such as nylon, acetal (Delrin.RTM.) or polycarbonate. The cannula carrier 412 and the trocar carrier 474 may be made of COP, polypropylene or other similar drug-compatible material. The trocar seal 480 and the cannula seal 430 may be made of elastomer, rubber, such as silicone rubber or bromobutyl rubber, or other relatively conformable sealing material that is also drug-compatible.

As mentioned above, FIGS. 5A-5D show the insertion assembly 400 in state two, the cocked position (e.g., before the user remotely activates the trigger assembly 304 to cause the cannula carrier 412 to drive the cannula 441 into an inserted position). Before insertion, the cannula carrier 412 is supported on the support ledge 422 of the guide housing 420 (best seen in FIG. 5D), which in turn holds the main insertion spring 410 in a compressed state. Note that the guide housing 420 does not move during cannula insertion.

Activation of the trigger assembly 304 causes the cannula carrier 412 to rotate such that the carrier tabs 413 move away from the support ledge 422 and align with slots 424 in the guide housing 420 (shown in FIGS. 4B, 5A, and 5C). While the cannula carrier 412 is shown rotating counterclockwise to release, in other embodiments the cannula carrier may rotate clockwise to release (in such embodiments, the slots 424 may be disposed immediately to the left of the tabs 413). Once the cannula carrier 412 is no longer supported by the guide housing ledge 422, the cannula carrier 412 can no longer resist the force of the main insertion spring 410, and the elastic energy contained in the main insertion spring 410 is converted to motion. The main insertion spring 410 drives the cannula carrier 412 with the attached cannula 441, the trocar carrier 474 with the attached trocar 447, the trocar seal 480, and the trocar retraction spring 482 downward. As these components move downward, the sharp distal tip of trocar 447, which extends slightly beyond the distal end of the cannula 441, penetrates the user's skin, and the cannula 441, which surrounds trocar 447, is inserted so the end of the cannula 441 is about 6 mm below the surface of the user's skin. At this point, the insertion assembly 400 is in state three, as seen in FIGS. 6A and 6B.

Figure 6A:
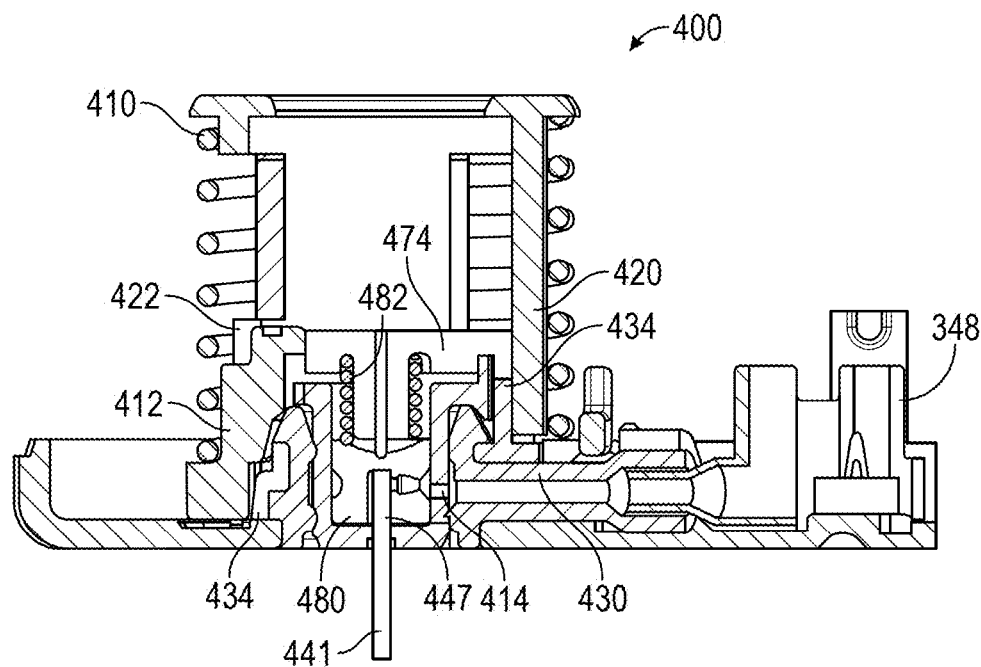
FIG. 6A is a section view of the components of FIG. 5D, shown in state three, after cannula insertion but before trocar retraction.
Figure 6B:
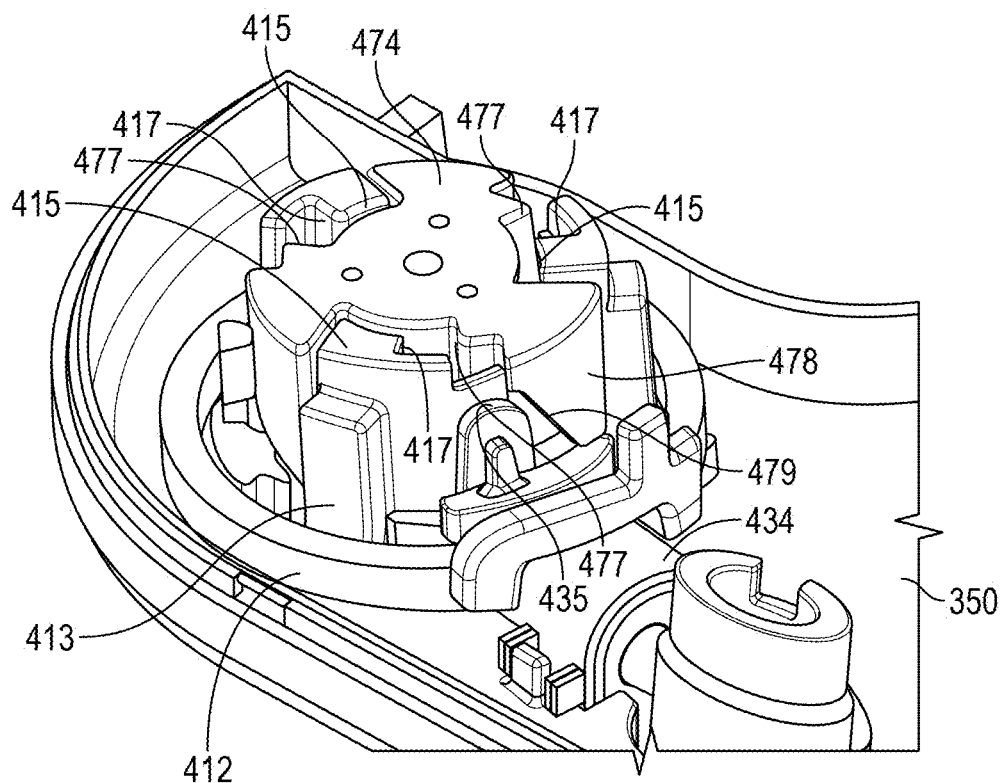
FIG. 6B is a perspective view showing additional components for use with the components of FIG. 6A, shown in position after cannula insertion but before trocar retraction.
Figure 7A:
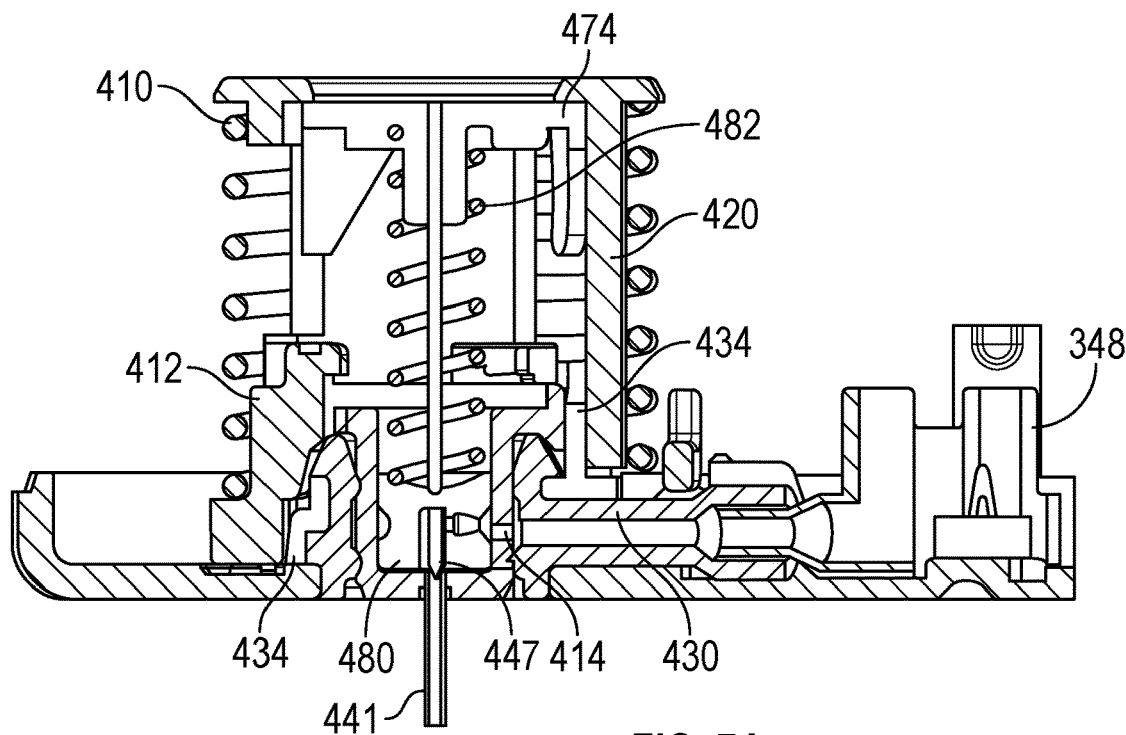
FIG. 7A is a section view of the components of FIGS. 5D and 6A, shown in state four, after cannula insertion and after trocar retraction.
Figure 7B:
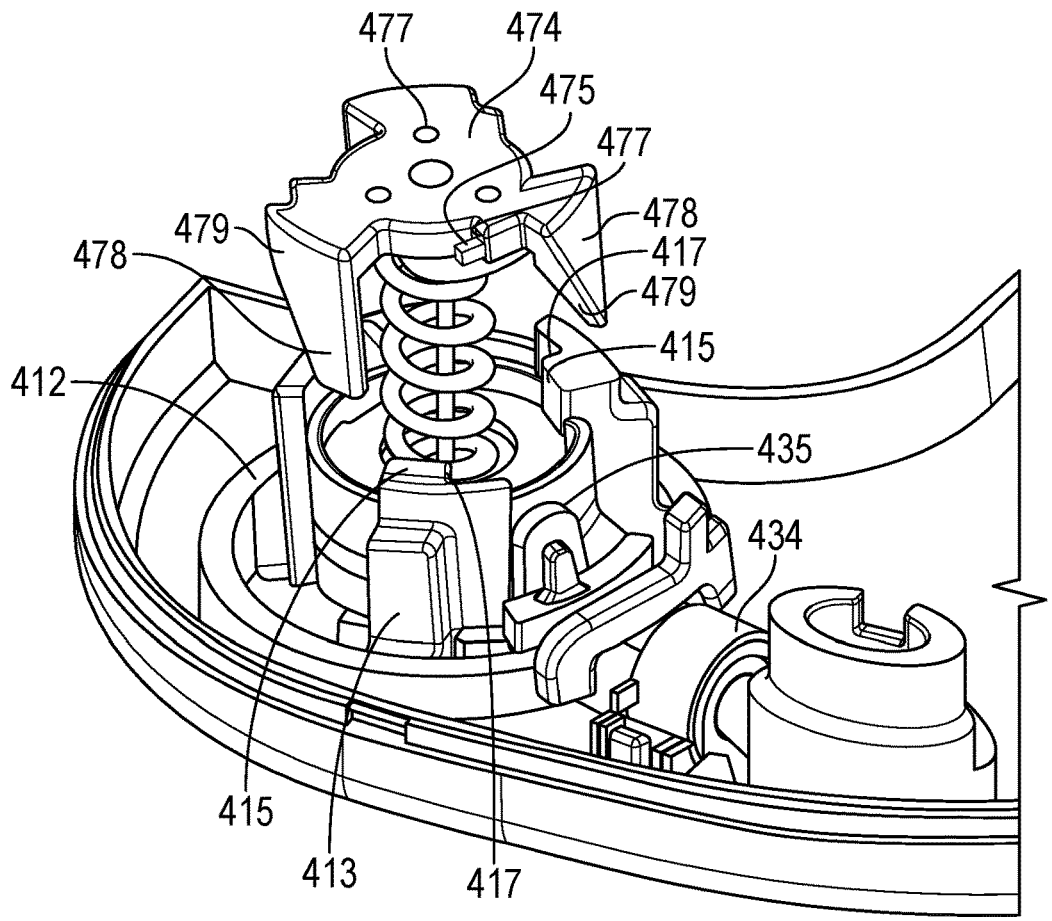
FIG. 7B is a perspective view showing additional components for use with the components of FIG. 7A, shown in position after cannula insertion and after trocar retraction.

As best seen in FIGS. 5B, 6B, and 7B, the cannula carrier 412 and the trocar carrier 474 include features to lock them together before and during cannula insertion. The trocar carrier 474 includes locking ledges 475 (labeled in FIG. 7B only) that fit beneath locking bosses 415 (FIGS. 6B and 7B only) on the cannula carrier 412. When the cannula carrier 412 and the trocar carrier 474 are locked together, the trocar retraction spring 482 is held in a compressed state. In addition, the trocar carrier 474 includes locking ledge walls 477 that contact locking boss walls 417 on the cannula carrier 412. These walls ensure that the trocar carrier 474 moves together with the cannula carrier 412 (e.g., only counter-clockwise, or whatever rotational direction the cannula carrier 412 is moving), so trocar carrier's locking ledges 475 cannot accidently slide out from under the cannula carrier's locking bosses 415 and unintentionally trigger penetration of the trocar 447.

Once the cannula carrier 412 and trocar carrier 474 are rotated to begin cannula insertion and move downward toward the user, angled edges 479 of tabs 478 on the trocar carrier 474 contact corners 435 on the seal retainer 434. As the trocar carrier 474 moves downward, the contact between the corners 435 and the angled edges 479 causes the trocar carrier 474 to rotate further and further (e.g., counter-clockwise) during cannula insertion. As the cannula carrier 412 moves downward, the carrier tabs 413 become aligned with slots 424 in the guide housing 420 (shown in FIGS. 4B, 5A, and 5C), thereby allowing the cannula carrier 412 to slide downward while preventing additional rotation of the cannula carrier 412. As the trocar carrier 474 rotates further counter-clockwise, the trocar carrier's locking ledges 475 slide out from under the cannula carrier's locking bosses 415.

FIGS. 6A and 6B show the insertion assembly 400 in state three: FIG. 6A shows the main insertion spring 410 fully fired, the cannula carrier 412 fully down, and the cannula 441 fully inserted, at the instant the trocar carrier 474 is released and before the trocar retraction spring 482 drives the trocar carrier 474 and the trocar 447 upward. (As shown, the skin is pierced at about 90 degrees and the end of the cannula is positioned about 6 mm below the surface of the skin.) FIG. 6B shows the same instant, with the main insertion spring 410 and the guide housing 420 removed. This view shows the moment the trocar carrier's locking ledges 475 are released from under the cannula carrier's locking bosses 415.

Once the trocar carrier's locking ledges 475 are released from under the cannula carrier's locking bosses 415 (this is also the moment that the cannula 441 is fully inserted, and the insertion assembly 400 is in state three, as seen in FIGS. 6A and 6B), the trocar carrier 474 can no longer resist the force of the trocar retraction spring 482. The elastic energy contained in the trocar retraction spring 482 is converted to motion, and the trocar retraction spring 482 drives the trocar carrier 474 with the attached trocar 447 upward. As the trocar carrier 474 moves upward, the trocar 447 is removed from the user and retracted back into the insertion assembly 400, leaving the cannula 441 inserted. This is state four, as seen in FIGS. 7A-7D.

Figure 7C:
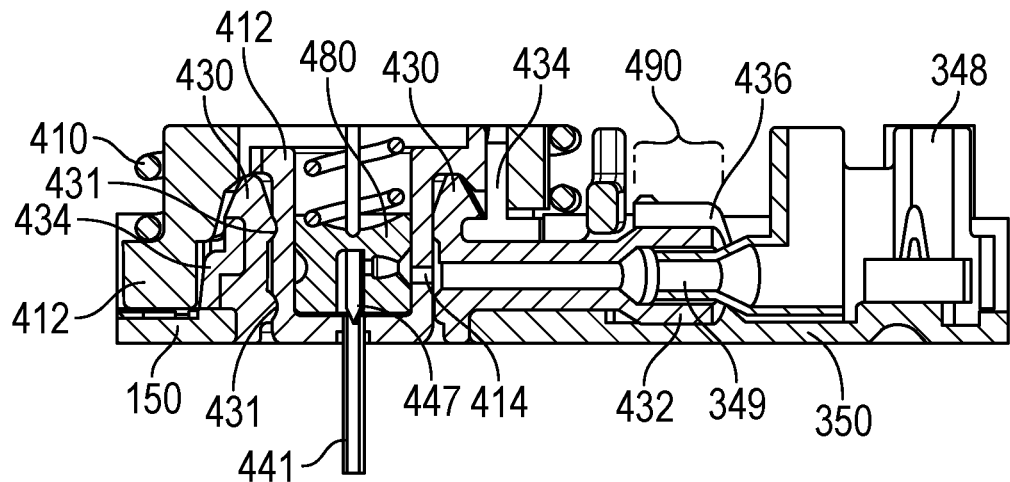
FIGS. 7C and 7D are section views of certain components of the assembly of FIG. 7A.

FIG. 7A is a section view showing the insertion assembly 400 fully fired and the trocar 447 fully retracted. FIG. 7B shows more details of the fully fired insertion assembly 400, with the main insertion spring 410 and the guide housing 420 removed. This is the position of the components of insertion assembly 400 while the device 100 is in use (e.g., during fluid delivery) by the user. The medicament path is best seen in FIGS. 7A and 7C. Broadly stated, medicament flows from the reservoir (not shown), to the outlet fitting 348, into a channel in the cannula seal 430, through a channel 414 in cannula carrier 412, through the trocar seal 480, and into the cannula 441 for delivery to the user.

Figure 7D:
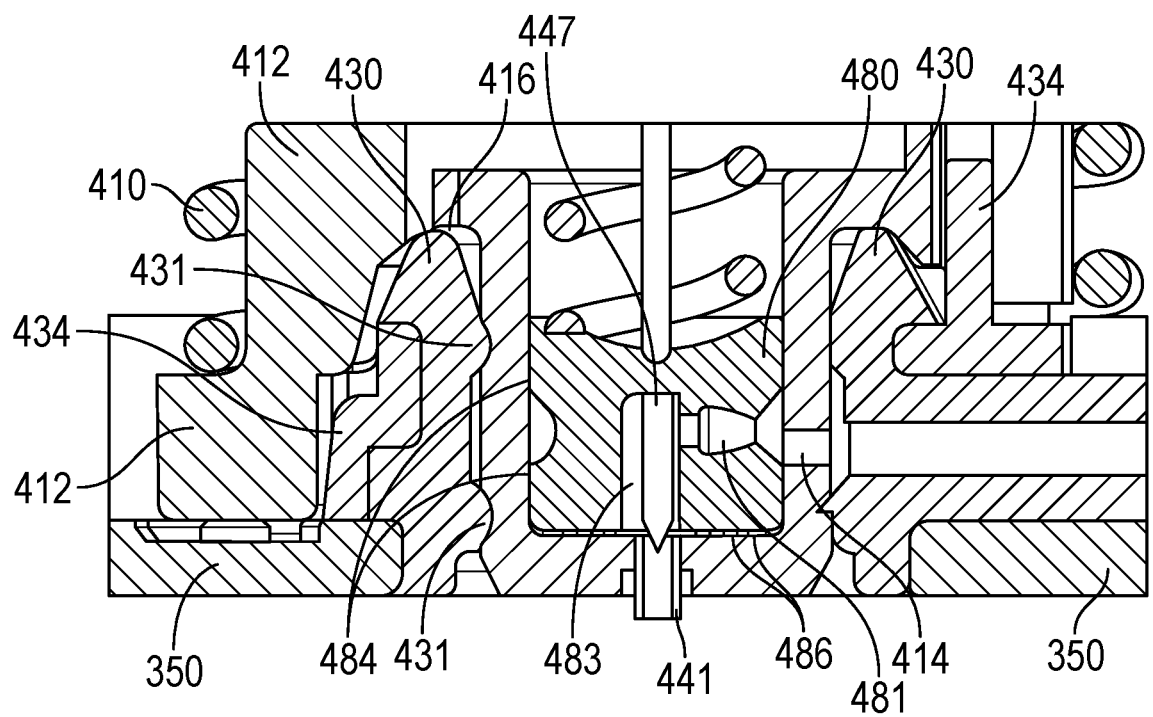

Best seen in FIGS. 7C and 7D is the highly efficient radial compression hydraulic seal formed between the cannula carrier 412 and the upper and lower seal rings 431 of the cannula seal 430. The upper and lower seal rings 431 can be separated by about 2.5 mm. Tapering of the cannula seal 430 to the small contact areas of the seal rings 431 concentrates surface stresses where the seal rings 431 contact the cannula carrier 412, to provide a good seal. Additional upper and lower seal rings are possible, but could increase space requirements. To enhance the seal at the seal rings 431, the main insertion spring 410 exerts force on the cannula carrier 412, holding it down against the baseplate 350 and causing an internal surface 416 of the cannular carrier 412 to push on the top surface of the cannula seal 430, as described in more detail below.

During the transition from state two to state three of insertion, the internal surface 416 of the cannula carrier 412 begins contacting the top of the cannula seal 430 before the bottom surface of the cannula carrier 412 contacts the baseplate 350. When state three is reached, the bottom surface of the cannula carrier 412 is held against the baseplate 350 and the cannula seal 430 is compressed from above. The high-energy main insertion spring 410 improves sealing reliability, and the cannula seal 430 acts as a bumper as it is compressed, helping dissipate the energy of insertion. Rather than being wasted, or converted to user-perceptible noise and feeling, residual energy from firing of the main insertion spring 410 is converted from kinetic energy to enhanced radial compression of the cannula seal 430.

In addition, the contact between the internal surface 416 of the cannula carrier 412 and the top surface of the cannula seal 430 forms a secondary face seal. In state three, the main insertion spring 410 continues pushing down on the cannula carrier 412, with approximately 7-10 N of force. This force, spread over the top surface of the cannula seal 430, results in a fluid seal capable of sealing approximately 3 bar, in addition to the seal maintained at the upper seal ring 431.

To further enhance this seal, the seal retainer 434 provides radial support, acting as a fixed backing ring/clamp, increasing the radial compression around the cannula seal 430. Even further enhancing the seal, the cannula carrier 412 provides additional radial compression with clamping force on the cannula seal 430, acting as an additional backing ring/clamp. The 7-10 N residual force derived from the main insertion spring 410 results in downward (axial) compression on the cannula seal 430, causing radial deformation of the cannula seal 430, further improving the seal formed between the cannula carrier 412 and the seal rings 431. In state three, since the cannula seal 430 is radially constrained by the seal retainer 434 and the cannula carrier 412, axial compression of the cannula seal 430 causes radial deformation of the seal 430, increasing the sealing force on the sealing rings 431. All of this results in a highly efficient and reliable hydraulic cannula seal.

Turning now to FIG. 7C, the medicament path also includes a compression-type fitting 490 formed from a clamp-portion 436 of the seal retainer 434 clamping ferrule 432 of the cannula seal 430 down onto barb 349 of outlet fitting 348. As an alternative, a separate component can be utilized to deliver the clamping forces provided by the clamp-portion 436 of the seal retainer 434. In addition, the ferrule 432 of the cannula seal 430 and the barb 349 of the outlet fitting 348 can be separate ferrule and barb components, but would introduce additional component interfaces along the medicament path, each requiring additional sealing features. In the configuration shown, the cannula seal 430 seals the cannula 441, absorbs energy during firing by compressing when struck by the cannula carrier 412, and helps seal the reservoir 336 with the ferrule 432.

As best seen in FIG. 7D, the medicament next flows through the ferrule 432, through the cannula seal 430, through the channel 414 in the cannula carrier 412, through the trocar seal inlet 481, through the trocar seal channel 483, and through the cannula 441 for delivery to the user. As can be seen from comparing FIGS. 5D, 6A, and 7A, the trocar seal 480 remains in one position within the cannula carrier 412 before, during, and after the insertion process, and remains in that position during user use of the device 100. The trocar seal 480 includes sidewall seal rings 484 and base seal rings 486. The sidewall seal rings 484 prevent medicament leakage into the cannula carrier 412 and, ultimately, into the device 100. The base seal rings 486 prevent leakage from around the cannula 441, and ensure that medicament flowing from the trocar seal inlet 481 and through the trocar seal channel 483 is directed into the cannula 441. FIG. 7D shows a pair of the sidewall seal rings 484 and a pair of the base seal rings 486, but additional seals may be used for additional leak protection.

The insertion assembly 400 provides a highly efficient, highly reliable medicament seal with low insertion forces, all in a compact space. The energy supplied to insert the cannula 441 is provided by the main insertion spring 410, and sufficient to:

allow the trocar 447 to quickly and cleanly pierce the user's skin for cannula insertion;

overcome friction forces during movement of the cannula carrier 412 surfaces against the cannula seal 430 surfaces and the seal retainer 434 surfaces; and result in compression and radial forces making a reliable medicament seal.

Excess energy is absorbed by compression of the cannula seal 430, which radially expands the cannula seal 430, increasing the radial forces exerted by the seal rings 431 against the surface of the cannula carrier 412 and exerted by the cannula seal 430 against the seal retainer 434, as explained in more detail below. Energy requirements and expenditures are also described in more detail presently.

During operation, as the insertion assembly 400 transitions from state two to state three, the radial compression forces exerted on the cannula seal 430 increase. As the cannula carrier 412 moves downward, it contacts the upper cannula seal ring 431, and, generally, causes the cannula seal 430 to be captured and surrounded between the surfaces of the cannula carrier 412 and the seal retainer 434. The seal retainer 434 acts as a fixed backing ring, providing radial support for the cannula seal 430, contributing to the radial clamping forces applied to the cannula seal 430. However, in some alternatives, there may be a small gap between the seal retainer 434 and the cannula seal 430 until the cannula seal 430 is compressed downward and expanded radially, as explained momentarily. The radial forces applied to the cannula seal 430 increase as the cannula carrier 412 continues moving downward, since the amount of contact, and therefore radial force, continues increasing between (i) the surfaces of the cannula carrier 412 and the cannula seal rings 431, (ii) the seal retainer 434 and the cannula seal 430, and (iii) in some alternatives, the surfaces of the cannula carrier 412 and the seal retainer 434. Contact between the cannula carrier 412 and the seal rings 431 during transition from state two to state three is also described in more detail below, in relation to the next embodiment.

As the cannula carrier 412 continues moving downward, contact is made between the top surface of the cannula seal 430 and the carrier internal surface 416 (see FIGS. 5D and 7D). As explained above, this contact occurs while the cannula carrier 412 is still moving downward. Therefore, as the cannula carrier 412 continues moving downward, the internal surface 416 of the cannula carrier 412 exerts increasing downward force on the cannula seal 430, and as it does, the cannula seal 430 is increasingly compressed as the cannula carrier 412 continues moving. As the carrier internal surface 416 pushes more and more on the cannula seal 430 from above, the cannula seal 430 expands more and more radially, resulting in additional radial compression forces between (i) the seal rings 431 and the cannula carrier 412 and (ii) the cannula seal 430 and the seal retainer 434. The cannula seal 430 may ultimately radially expand by, for instance, 0.5 mm. (In some alternatives, a small gap between the seal retainer 434 and the cannula seal 430 may decrease until it is eliminated as the cannula seal 430 expands radially due to downward compression of the cannula seal 430 by the internal surface 416 of the cannula carrier 412.) In addition, as described above, contact between the internal surface 416 of the carrier 412 and the top surface of the cannula seal 430 forms a secondary face seal. As such, a highly efficient and highly reliable cannula seal is achieved by (1) this face seal formed at the internal surface 416 of the cannula carrier 412 and the top surface of the cannula seal 430, (2) contact between the seal rings 431 and the cannula carrier 412, (3) radial clamping forces exerted on the cannula seal 430 by the seal retainer 434, (4) increased radial clamping forces exerted by the cannula carrier 412, acting as an additional backing ring (in addition to seal retainer 434) and providing increased radial compression of the cannula seal 430, and (5) downward force exerted on the top of the cannula seal 430 by the cannula carrier 412 at the internal surface 416 of the cannula carrier 412, which expands the cannula seal 430 radially and increases the radial forces exerted (a) by the seal rings 431 against the surface of the cannula carrier 412 and (b) by the cannula seal 430 against the seal retainer 434.

I. Selected Embodiments of Trigger Assemblies

FIGS. 8-12B illustrate representative examples of disposable assemblies 800, 900, 1000, and 1100 with remotely actuatable trigger assemblies of various configurations in accordance with embodiments of the present technology. The features of the disposable assemblies 800, 900, 1000, and 1100 can be generally similar to the features of the disposable assembly 300 of FIGS. 1A-7D. Accordingly, like numbers are used to identify similar or identical components in FIGS. 1A-7D, and the discussion of the disposable assemblies 800, 900, 1000, and 1100 of FIGS. 8-12B will be limited to those features that differ from the disposable assembly 300 of FIGS. 1A-7D. Additionally, any of the features of the disposable assemblies 800, 900, 1000, and 1100 of FIGS. 8-12B can be combined with each other and/or with the features of the disposable assembly 300 of FIGS. 1A-7D.

Figure 8:
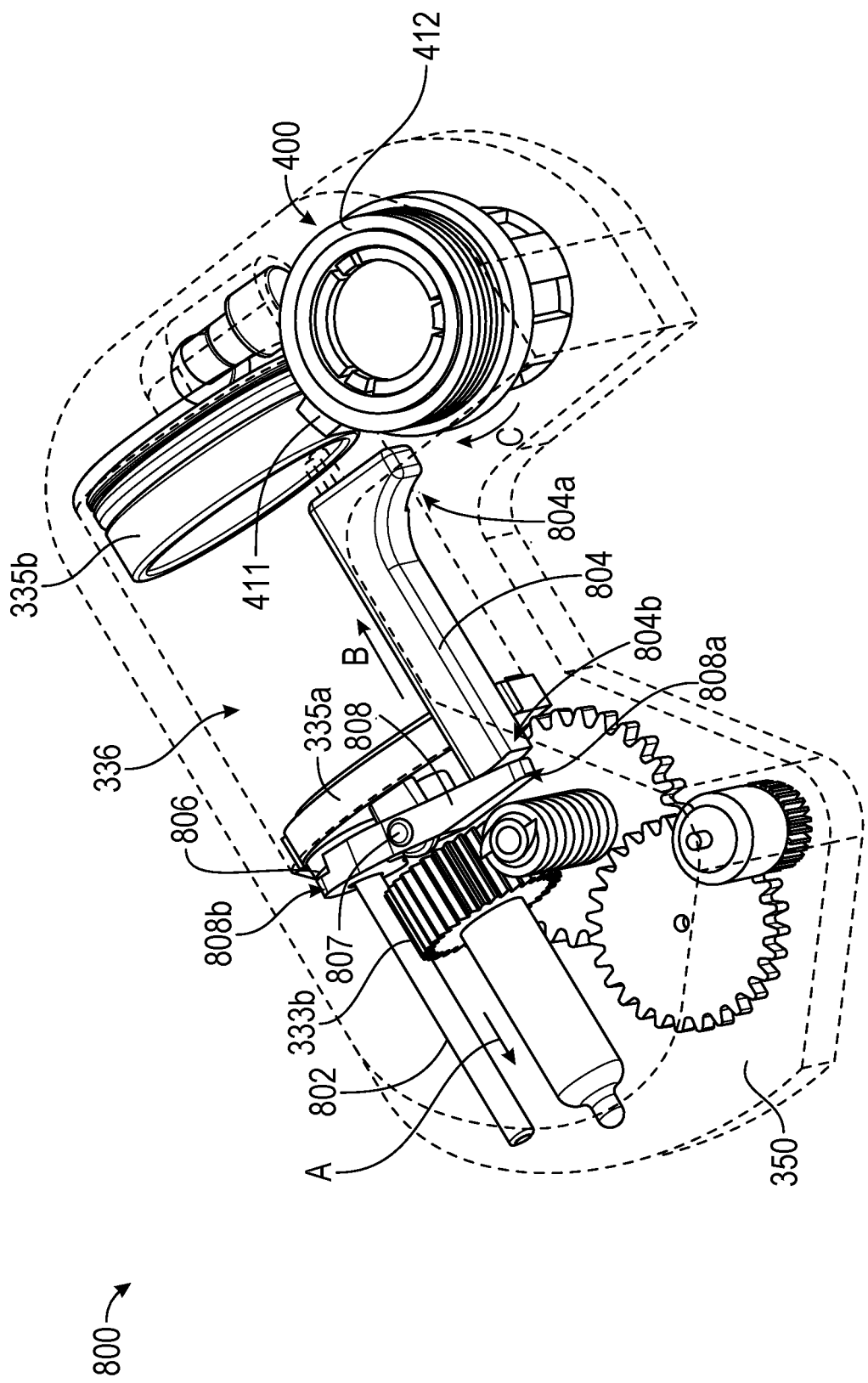
FIG. 8 is a perspective view of a disposable assembly configured in accordance with several embodiments of the present technology.

In any of the infusion device embodiments disclosed herein, the trigger assembly 304 can be configured to push or pull a portion of the cannula carrier 412 to cause the tabs 413 of the cannula carrier 412 to rotate into alignment with the slots 424 (FIG. 4B) in the guide housing 420. For example, FIG. 8 shows a disposable assembly 800 having a trigger assembly coupled to the drive assembly 329 of the reservoir assembly. The trigger assembly can comprise a shaft 802, a rod 804, a clutch disc 806, and a lever 808. The rod 804 has a first end portion 804a adjacent the trigger boss 411 of the cannula carrier 412 and a second end portion 804b adjacent the lever 808. The lever 808 can be coupled to a stationary portion of the reservoir assembly via a pin 807, and has first and second lever arms 808a, 808b that are configured to rotate about the pin 807. The lever 808 does not translate forward when the plunger pusher 335a translates forward. The first lever arm 808a is positioned adjacent an end of the rod 804 and, when the trigger assembly is activated, the first lever arm 808a rotates in a counterclockwise direction, thereby pushing the rod 804 forward, towards the trigger boss 411 of the cannula carrier 412 (as indicated by arrow B). The clutch disc 806 is disposed at the second lever arm 808b. The shaft 802 has a first end (not visible) fixed to the plunger pusher 335a (or another component that moves with the plunger plusher 335a) and a second, free end. As the shaft 802 extends rearwardly from the plunger pusher 335a, it passes through an opening in the clutch disc 806 disposed at the second lever arm 808b.

When the drive assembly 329 of the reservoir assembly operates in a forward direction (for example, during a plunger seek operation), the shaft 802 translates forward with the plunger pusher 335a. The clutch disc 806 allows the shaft 802 to pass therethrough in this forward direction. However, when the motor is reversed (for example, after a plunger seek operation is complete) and the plunger pusher 335a moves in a rearward direction, the clutch disc 806 clamps down on the shaft 802 and prevents rearward translation of the shaft 802 through the clutch disc 806. As a result, the shaft 802 becomes a substantially rigid body with the second lever arm 808b such that the shaft 802 pulls the second lever arm 808b counterclockwise about the pin 807. This rotation of the second lever arm 808b causes rotation of the first lever arm 808a, which engages the second end portion 804b of the rod 804 to push the rod 804 forward (as indicated by arrow B). Forward translation of the rod 804 forces the first end portion 804a of the rod 804 into contact with the trigger boss 411 of the cannula carrier 412 and pushes the cannular carrier 412 clockwise (as indicated by arrow C) to trigger cannula insertion.

In use, the user positions the device (including the disposable assembly 800) on the skin with the trigger assembly in a locked state. Once the device is adhered to the user's skin (e.g., after the plunger seek operation is complete and the PBUP108 is removed), the user can trigger cannula insertion by interfacing with a remote controller to indicate a desire to trigger cannula insertion. The user may, for example, press a button on the touchscreen of the user's mobile device. In response to the user's indication, the remote controller may communicate a command to the device (for example, via the microprocessor of the durable assembly 200) that causes the motor to run in reverse. In response to the reversed motor, the plunger pusher 335a moves rearwardly, thus rotating the lever 808 and, via translation of the rod 804, forcing the tabs 413 of the cannula carrier 412 to rotate into alignment with the slots 424 of the guide housing 420 for cannula insertion. After triggering, the plunger pusher 335a is advanced back into contact with the plunger 335b to begin delivery of the medicament.

In some embodiments of the disposable assembly 800, the rod 804 is configured to pull on the trigger boss 411 rather than push as detailed above. For example, the first end portion 804a of the rod 804 may be positioned to the right of the trigger boss 411 and connected thereto via one or more linkages.

According to several embodiments, the cannula carrier 412 of the insertion assembly 400 is biased towards rotating in a direction that would release the cannula carrier 412 from the guide housing 420. In such embodiments, the trigger assembly may comprise a blocking member that prevents such rotational motion until the user remotely activates the trigger assembly to remove the blocking member and release the cannula carrier 412. For example, the blocking member can engage a portion of the cannular carrier 412 (such as the trigger boss 411) to prevent rotation of the cannula carrier 412 in the direction of release. Remote activation of the trigger assembly causes the blocking member to disengage from the trigger boss 411, thereby allowing the cannula carrier 412 to rotate such that the tabs 413 on the carrier 412 align with the slots 424 in the guide housing 420. Alignment of the tabs 413 with the slots 424 enables the downward motion of the cannula carrier 412 and insertion of the cannula 441.

To rotationally bias the cannula carrier 412, the insertion assembly 400 may include a torsion spring. In some embodiments, the ledges 422 (see FIG. 4B) of the guide housing 420 can slant downwardly towards the slots 424 such that, when the blocking member is removed, the cannula carrier 412 can no longer resist the force of the main insertion spring 410, and the elastic energy contained in the main insertion spring 410 is converted to motion. Because of the slanted ledges 422, the cannula carrier 412 rotates as it moves downwardly until the tabs 413 sitting on the ledges 422 align with the slots 424 on the guide housing 420.

Figure 9A:
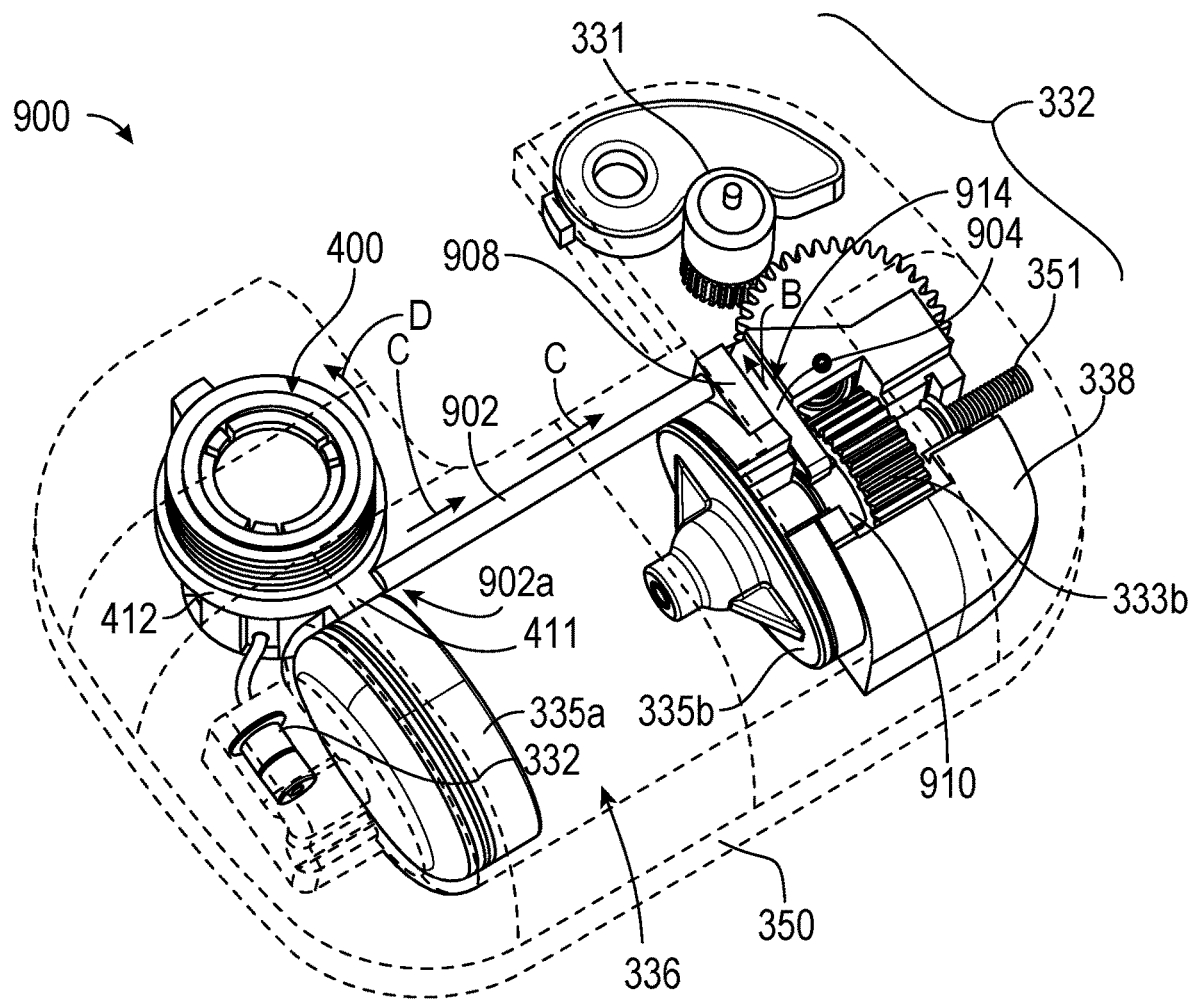
FIG. 9A is a perspective view of a disposable assembly configured in accordance with several embodiments of the present technology.
Figure 9B:
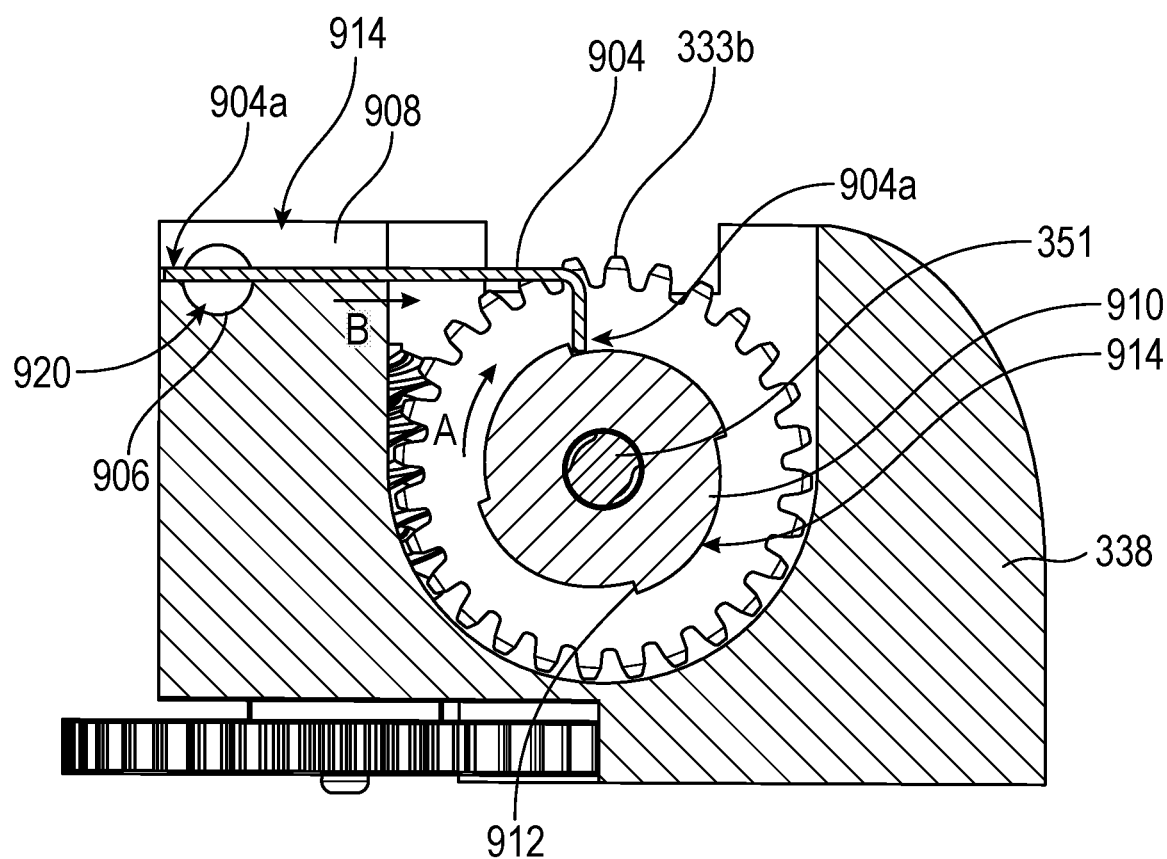
FIG. 9B is a section view of certain components of the disposable assembly of FIG. 9A.
Figure 9C:
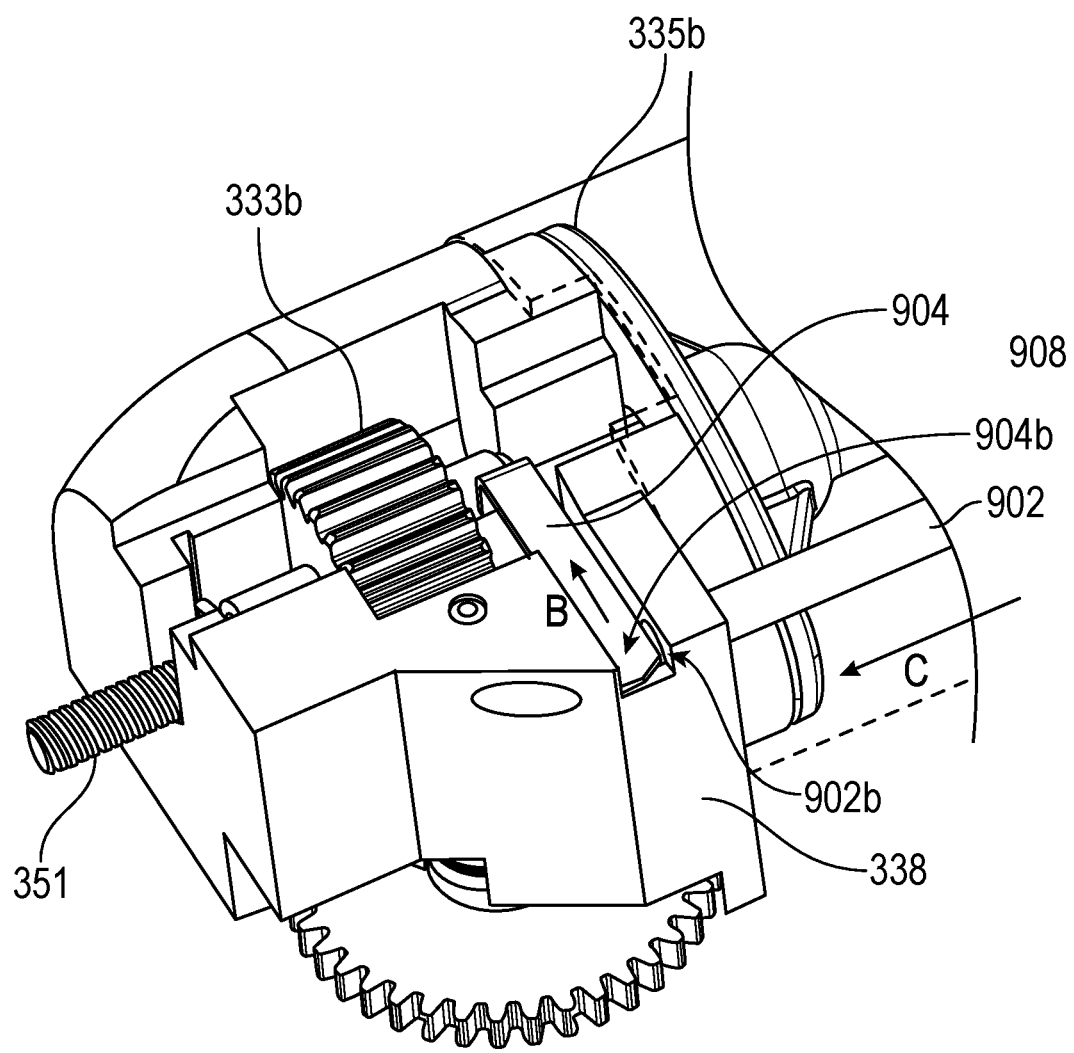
FIG. 9C is a perspective view of certain components of the disposable assembly of FIG. 9A.

FIGS. 9A-9C are different views of a disposable assembly 900 having a rotationally-biased cannula carrier 412 and a trigger assembly operatively coupled to the drive assembly 329. The trigger assembly can comprise a rod 902, a latch 904, and a ratchet wheel 910 coupled to the worm gear 333b of the reservoir assembly such that rotation of the worm gear 333b causes rotation of the ratchet wheel 910. The rod 902 has a first end 902a abutting the trigger boss 411 on the cannula carrier 412, and a second end 902b received within an opening 920 (FIG. 9B) in the reservoir support block 338. In some embodiments, for example as shown in FIGS. 9A-9C, the rod 902 is oriented parallel to a longitudinal axis of the reservoir 336. The reservoir 336, the reservoir support block 338, and/or another component of the disposable assembly 900 can include a groove 906 (FIG. 9B) configured to receive at least a portion of the rod 902 to guide translation of the rod 902 and prevent lateral movement (e.g., any movement that is not parallel to the longitudinal axis of the reservoir 336).

When the trigger assembly is in a locked state (preinsertion, as shown in FIGS. 9A-9C), translation of the rod 902 beyond the opening 920 (in a direction away from the insertion assembly 400) is prevented by a first end 904a of the latch 904. For example, the latch 904 can sit in a channel 914 in the support block 338 that positions the first end 904a of the latch 904 between the second end 902b (FIG. 9C) of the rod 902 and a backstop 908 on the support block 338. As previously described, the cannula carrier 412 can be biased towards rotating in a particular direction (here shown as counterclockwise, as indicated by arrow D), but is prevented from doing so by the rod 902 which is trapped between the trigger boss 411 on the cannula carrier 412 and the first end 904a of the latch 904. Because of the continuous force exerted on the rod 902 by the cannula carrier 412, the rod 902 is biased towards translating rearwardly (towards the support block 338, as indicated by arrow C), but is prevented from doing so by the presence of the first end 904a of the latch 904 across the opening 920.

A second end 904b of the latch 904 can be engaged with a tooth 912 (FIG. 9B) on the ratchet wheel 910. When the worm gear 333b rotates counterclockwise (for example, to advance the plunger pusher 335a forward during a plunger seek operation), the ratchet wheel 910 also rotates counterclockwise. During such rotation the teeth 912 of the ratchet wheel 910 do not engage the latch 904 so as to move the first end 904a of the latch 904 away from the opening 920. When the motor is reversed and the worm gear 333b runs clockwise (arrow A in FIG. 9B), the ratchet wheel 910 also rotates clockwise. During such rotation, one of the teeth 912 of the ratchet wheel 910 can engage the second end 904b of the latch 904 and pull the latch 904 in a direction away from the second end 902b of the rod 902 and the opening 920 (indicated by arrow B). Once the latch 904 has cleared the opening 920, the rod 902 is free to slide through the opening 920, which allows the cannula carrier 412 to rotate (indicated by arrow D). Rotation of the cannula carrier 412 aligns the tabs 413 on the carrier 412 with the slots 424 in the guide housing 420 (see FIG. 4B), thereby allowing the main spring 410 to push the cannula carrier 412 downwardly and insert the cannula 441.

In use, the user positions the device (including the disposable assembly 900) on the skin with the trigger assembly in a locked state. Once the device is adhered to the user's skin (e.g., after a plunger seek operation is completed, if needed, and the PBUP 108 is removed), the user can trigger cannula insertion by interfacing with a remote controller to indicate a desire to trigger cannula insertion. The user may, for example, press a button on the touchscreen of the user's mobile device. In response to the user's indication, the remote controller may communicate a command to the device (for example, via the microprocessor of the durable assembly 200) that causes the motor to run in reverse. In response to the reversed motor, the worm gear 333b and ratchet wheel 910 rotate clockwise, thus moving the latch 904 and allowing the cannula carrier 412 to drop for insertion. After triggering, the plunger pusher 335a is advanced back into contact with the plunger 335b to begin delivery of the medicament.

Figure 10A:
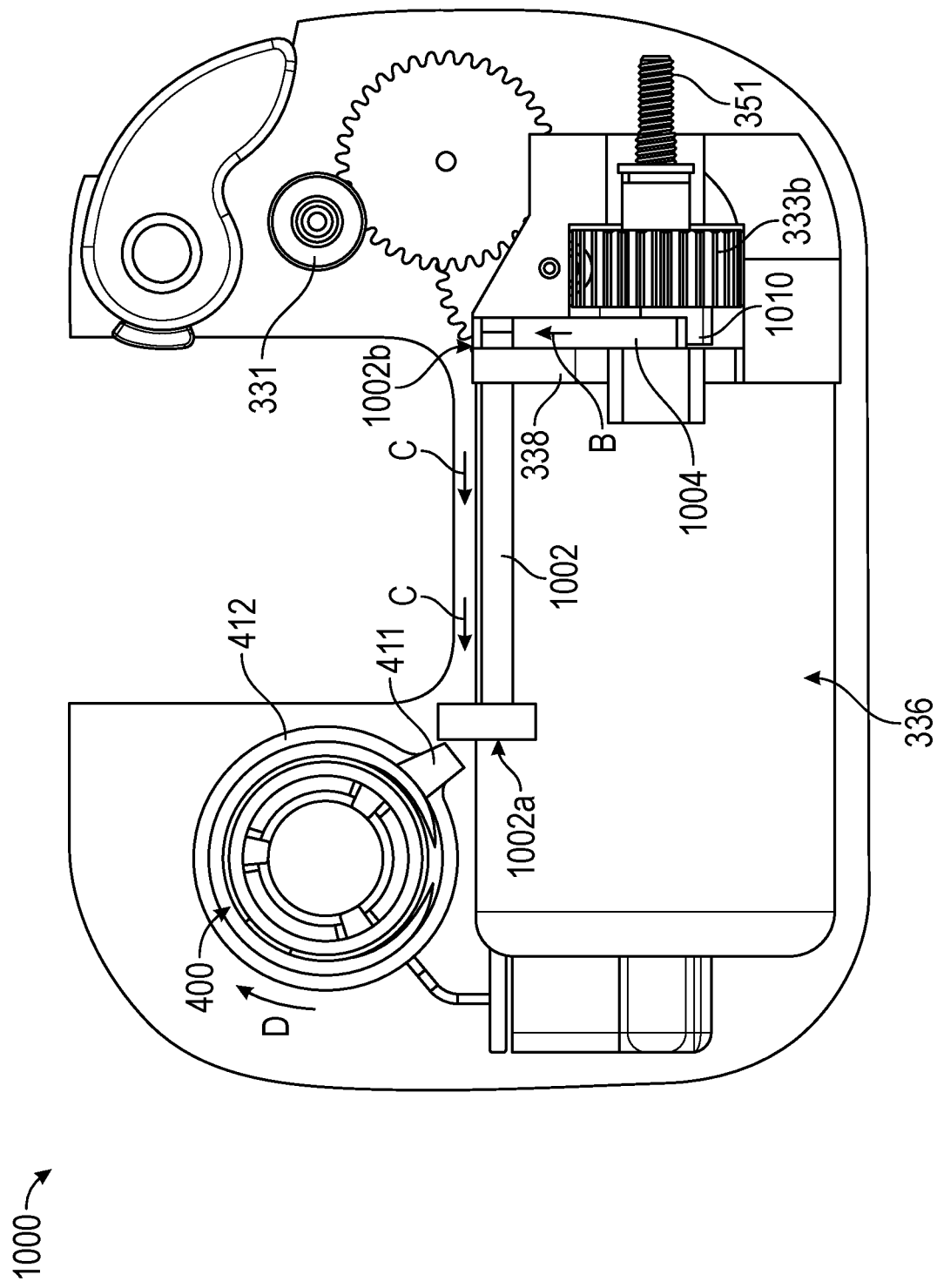
FIG. 10A is a perspective view of a disposable assembly configured in accordance with several embodiments of the present technology.
Figure 10B:
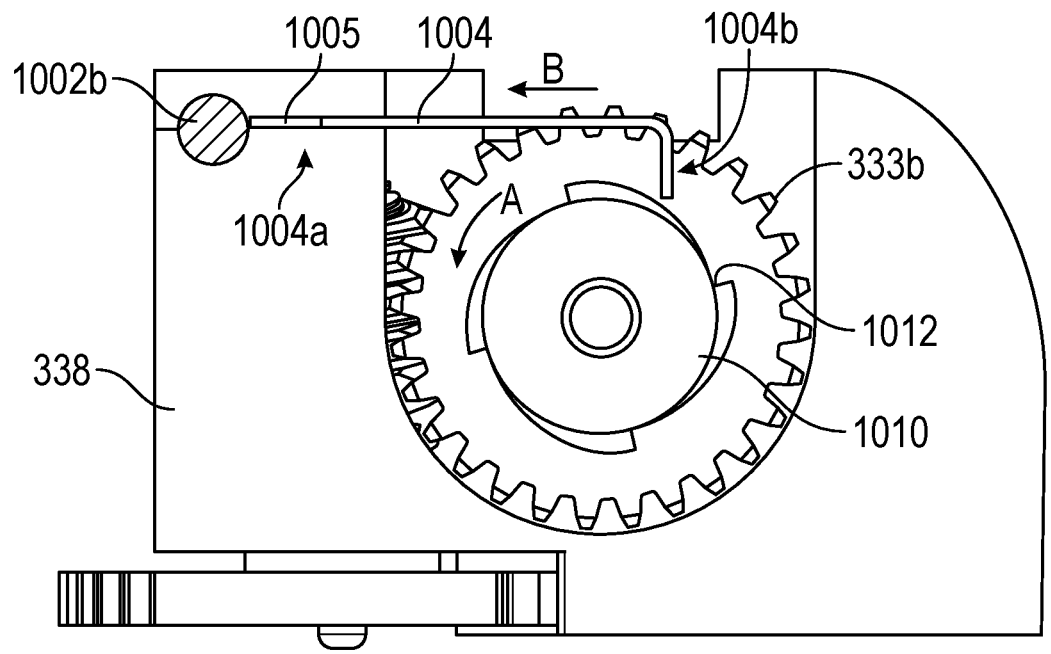
FIG. 10B is a section view of certain components of the disposable assembly of FIG. 9A.
Figure 10C:
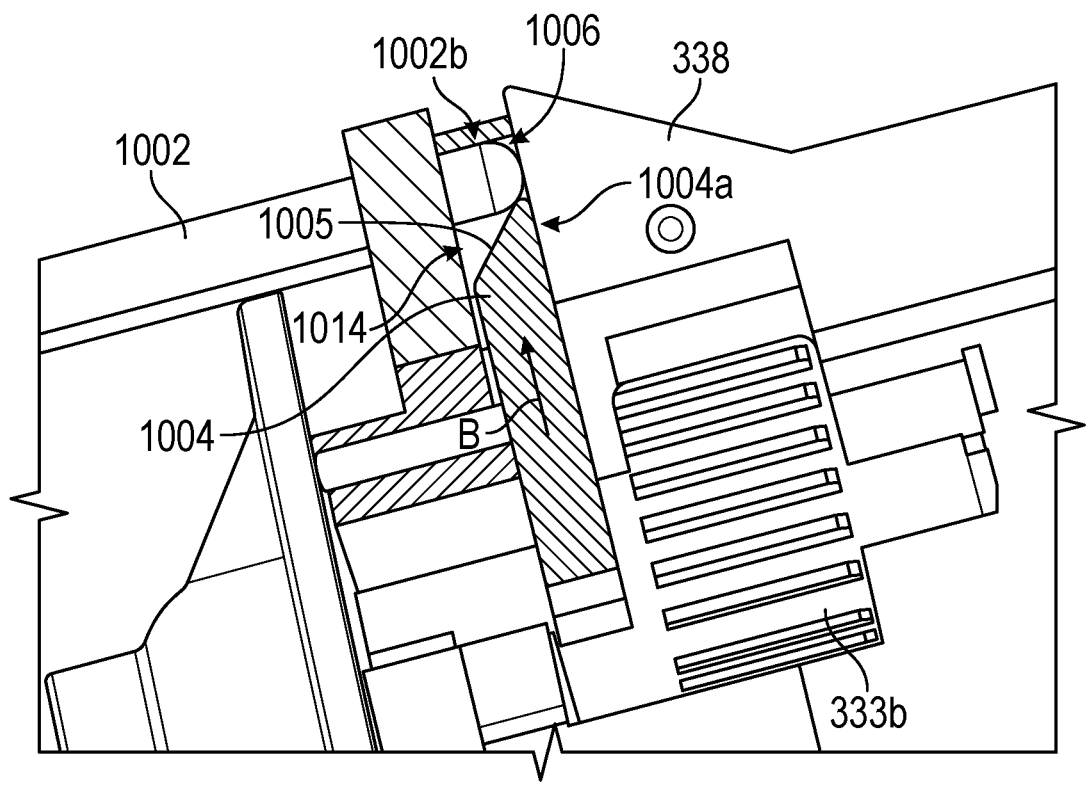
FIG. 10C is a perspective view of certain components of the disposable assembly of FIG. 9A.

FIGS. 10A-10C are different views of a disposable assembly 1000 having a trigger assembly operatively coupled to the drive assembly 329. In contrast to the disposable assembly 900 shown and described with respect to FIGS. 9A-9C, the cannula carrier 412 of the disposable assembly 1000 is not rotationally biased and requires forced rotation to trigger cannula insertion. The trigger assembly can comprise a rod 1002, a latch 1004, and a ratchet wheel 1010 coupled to the worm gear 333b such that rotation of the worm gear 333b causes rotation of the ratchet wheel 1010. The rod 1002 has a first end portion 1002a abutting the trigger boss 411 on the cannula carrier 412, and a second end portion 1002b received within an opening in the reservoir support block 338. In some embodiments, for example as shown in FIGS. 10A-10C, the rod 1002 is oriented parallel to a longitudinal axis of the reservoir 336. The reservoir 336, the reservoir support block 338, and/or another component of the disposable assembly 1000 can include a groove 1006 (FIG. 10C) configured to receive at least a portion of the rod 1002 to guide translation of the rod 1002 and prevent lateral movement (e.g., any movement that is not parallel to the longitudinal axis of the reservoir 336).

When the trigger assembly is in a locked state (preinsertion, as shown in FIGS. 10A-10C), the second end portion 1002b extends beyond the opening 920 in the reservoir support block 338 (in a direction away from the insertion assembly 400) and is adjacent a first end portion 1004a of the latch 1004. For example, the latch 1004 can sit in a channel 1014 in the support block 338. A second end 1004b of the latch 1004 can be engaged with a tooth 1012 (FIG. 10B) on the ratchet wheel 1010 such that when the ratchet wheel 1010 rotates in a counterclockwise direction (arrow A in FIG. 10B), the tooth 1012 pushes the latch 1004 towards the second end 1002b of the rod 1002 (indicated by arrow B). The counterclockwise direction can be the reverse of the normal direction of rotation of the motor, which in this case is in the clockwise direction. The latch 1004 can have a beveled end surface 1005 such that, as the latch 1004 engages the second end portion 1002b of the rod 1002, the beveled end surface 1005 pushes the rod 1002 forwardly (indicated by arrow C). Forward motion of the rod 1002 causes the first end portion 1002a to engage the trigger boss 411 and force rotation of the cannula carrier 412 (indicated by arrow D). Rotation of the cannula carrier 412 aligns the tabs 413 on the carrier 412 with the slots 424 in the guide housing 420 (see FIG. 4B), thereby allowing the main spring 410 to push the cannula carrier 412 downwardly and insert the cannula 441.

In use, the user positions the device (including the disposable assembly 1000) on the skin with the trigger assembly in a locked state. Once the device is adhered to the user's skin (e.g., after a plunger seek operation is completed, if needed, and the PBUP 108 is removed), the user can trigger cannula insertion by interfacing with a remote controller to indicate a desire to trigger cannula insertion. The user may, for example, press a button on the touchscreen of the user's mobile device. In response to the user's indication, the remote controller may communicate a command to the device (for example, via the microprocessor of the durable assembly 200) that causes the motor to run in reverse. In response to the reversed motor, the worm gear 333b and ratchet wheel 910 rotate counterclockwise, thus pushing the latch 1004 into engagement with the rod 1002. Thus, the rod 1002 moves in a forward direction and causes the tabs 413 of the cannula carrier 412 to rotate into alignment with the slots 424 in the guide housing 420, thereby triggering cannula insertion. After triggering, the plunger pusher 335a is advanced back into contact with the plunger 335b to begin delivery of the medicament.

Figure 11A:
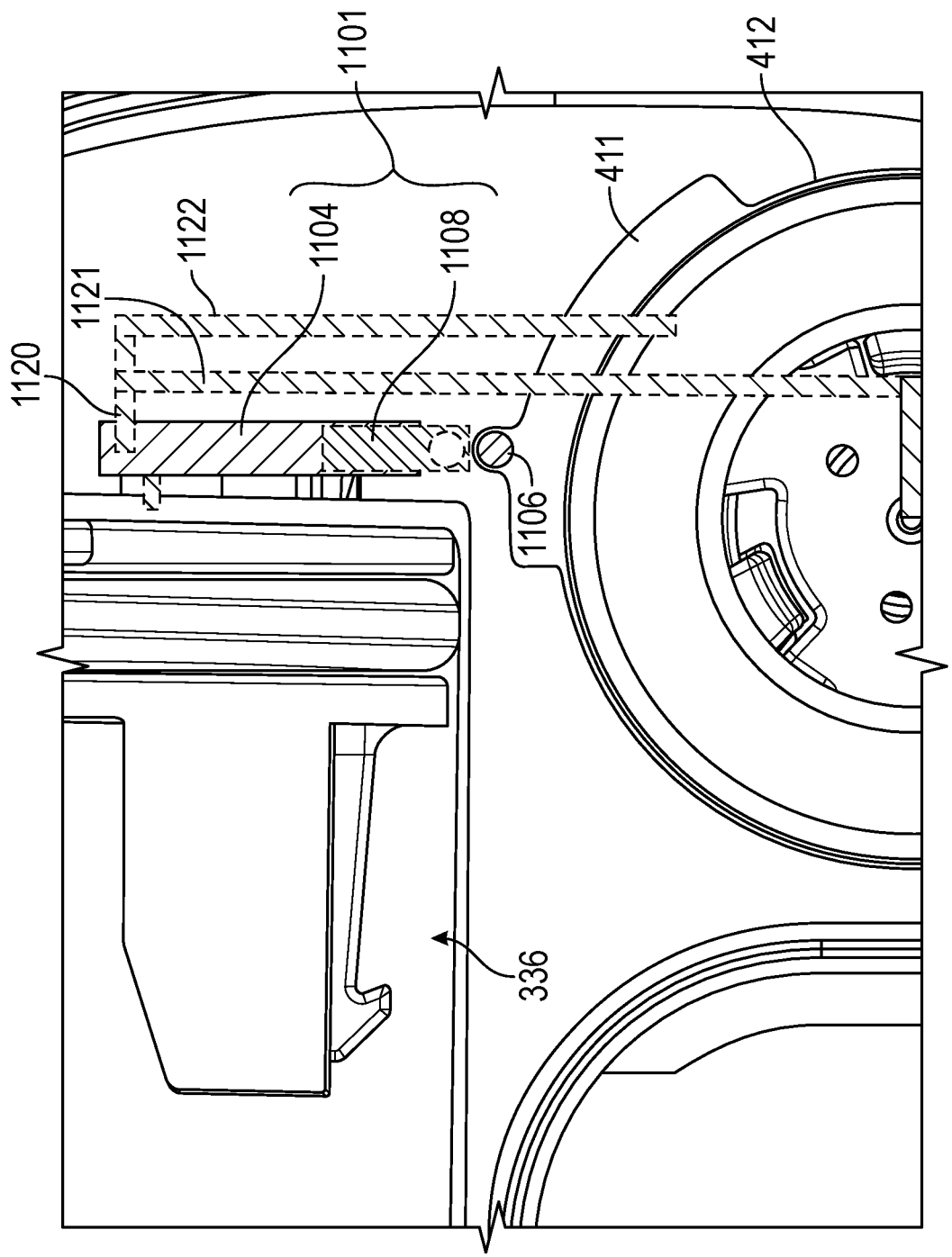
FIG. 11A is a top view of a portion of a disposable assembly configured in accordance with several embodiments of the present technology, shown in a first state before cannula insertion.

As previously mentioned, in some embodiments the cannula carrier 412 of the insertion assembly 400 is biased towards rotating in a direction that would cause cannula insertion. For example, a trigger assembly of the present technology can comprise a hydraulic trigger configured to permit movement of the cannula carrier 412. FIG. 11A shows a top view of a disposable assembly 1100 having a trigger assembly that includes a hydraulic slave cylinder 1101 configured to share a fluid connection with the reservoir 336. The slave cylinder 1101 can include a housing 1104, a piston 1108 at least partially positioned within the housing 1104, a seal 1112 (see FIG. 11B) between the piston 1108 and the housing 1104, and a spring-loaded pin 1106 positioned between an end portion of the piston 1108 and a portion of the cannula carrier 412. The piston 1108 can include a channel 1110 (see FIG. 11B) extending through its thickness and configured to receive at least a portion of the pin 1106.

Figure 11B:
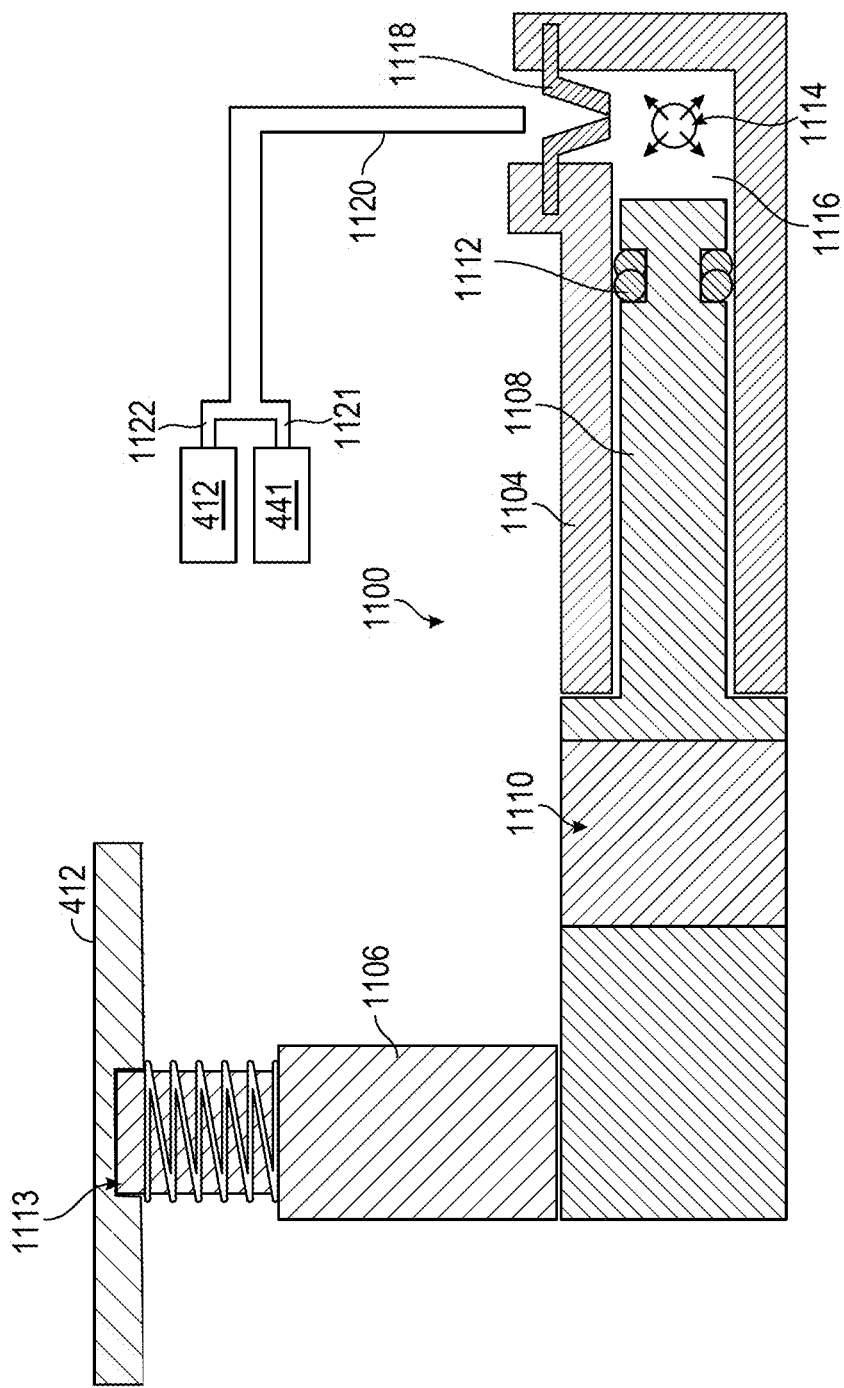
FIG. 11B schematically depicts a hydraulic trigger assembly of the disposable assembly of FIG. 11A.

Referring to FIG. 11B, the housing 1104 can have a first opening through which the piston 1108 extends, a second opening 1114 through which the housing 1104 is configured to share a fluid connection with the reservoir 336, and a third opening 1119 across which a valve 1118 is positioned. Medicament from the reservoir can flow into the housing 1104 through the second opening 1114 and into a space defined by the sidewalls of the housing 1104, the piston 1108, and the valve 1118.

Figure 12A:
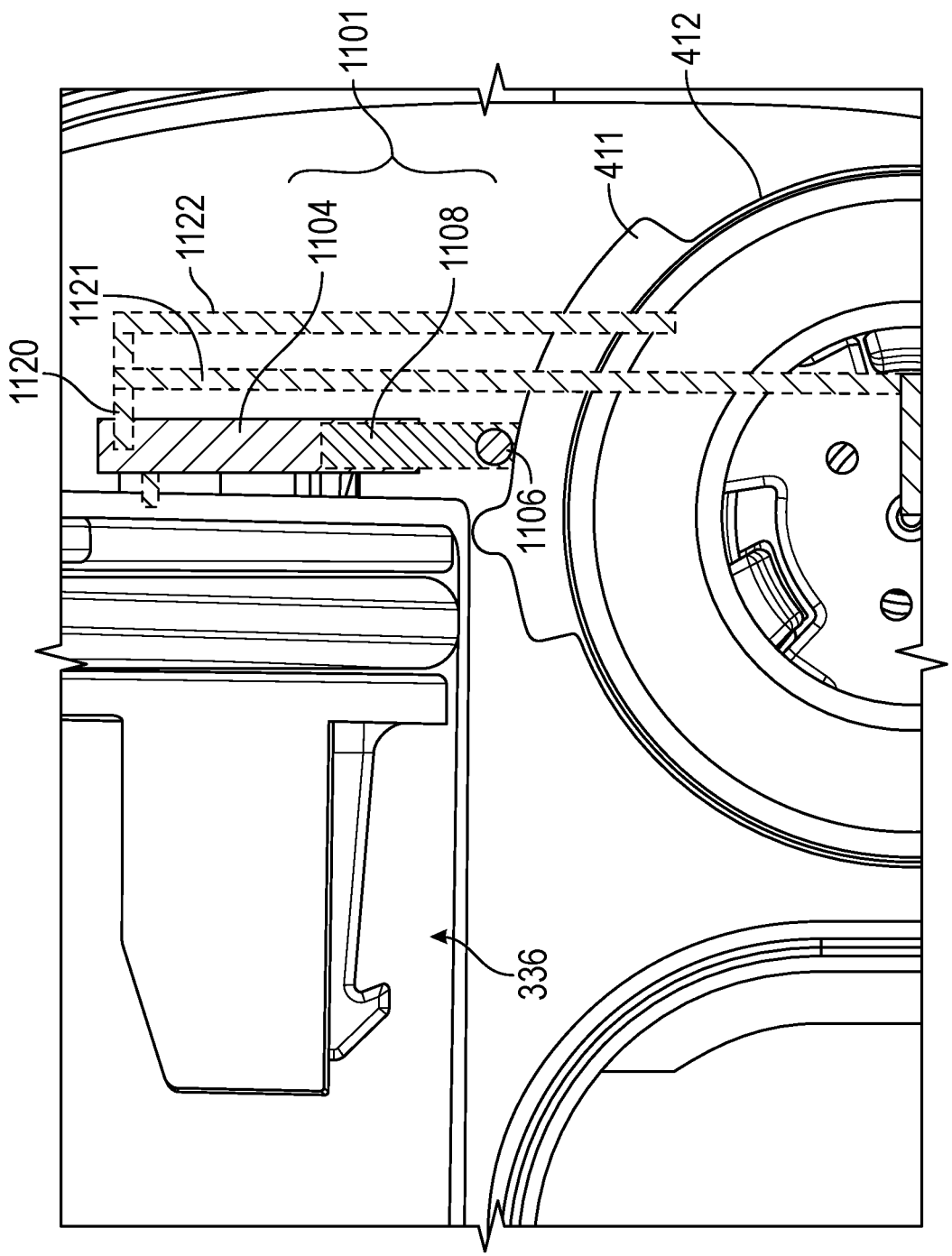
FIG. 12A is a top view of the portion of the disposable assembly of FIG. 11A, shown in a second state after cannula insertion.
Figure 12B:
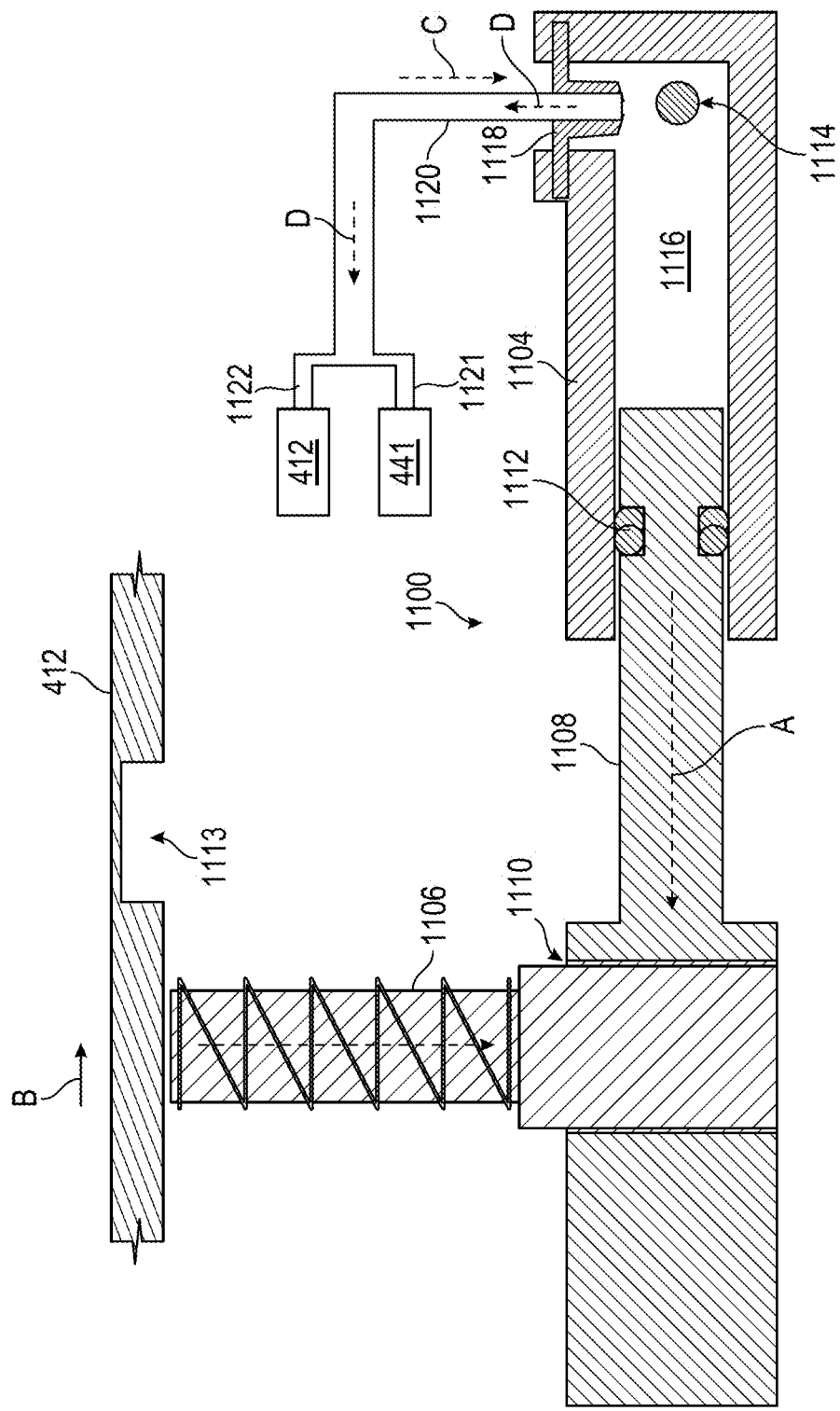
FIG. 12B schematically depicts the hydraulic trigger assembly of the disposable assembly of FIG. 12A.

In use, the user positions the device (including the disposable assembly 1100) on the skin with the trigger assembly in a locked state. Once the device is adhered to the user's skin (e.g., after a plunger seek operation is complete, if needed), the user can trigger cannula insertion by interfacing with a remote controller to indicate a desire to trigger cannula insertion. The user may, for example, press a button on the touchscreen of the user's mobile device. In response to the user's indication, the remote controller may communicate a command to the device that causes the motor to push the plunger forward and deliver medicament into the housing 1104. This delivery of medicament pushes the piston 1108 away from the housing 1104 such that the channel 1110 aligns with the spring-loaded pin 1106. As shown in FIGS. 12A and 12B, when the channel 1110 aligns with the spring-loaded pin 1106, the pin 1106 drops into the channel 1110, thereby disengaging the cannula carrier 412 and allowing the tabs 413 of the carrier 412 to rotate into alignment with the slots 424 in the guide housing 420. Now positioned in the channel 1110, the pin 1106 advantageously locks the piston 1108 in place to prevent excessive compliance.

In addition to inserting the cannula 441 into the patient, the downward motion of the cannula carrier 412 causes a tubular connector 1120 to pass through the valve 1118 and establish a fluid path between the reservoir 336 and the cannula 441. The valve 1118 can be a check valve and the downward motion of the connector 1120 can crack the check valve. Other means for establishing a fluid path between the cannula 441 and the reservoir 336 are possible. For example, the valve 1118 can be a septum and the tubular connector 1120 can be a needle that pierces the septum when the cannula carrier 412 drops. In some embodiments, the valve 1118 is a ball valve and establishing the fluid path comprises spinning the ball valve. In any case, use of a hydraulic trigger can advantageously obviate the need for the PBUP 108, as the outflow from the reservoir 336 is already contained by the hydraulic slave cylinder.

To prevent triggering the cannula release prematurely while filling the reservoir 336, the device can be configured such that the pressure required to push the piston 1108 is greater than the pressure to push the plunger 335b without using the motor. For example, the disposable assembly 1100 can be configured such that the piston friction is greater than the pressure attributable to filling the reservoir 336 with a syringe but still less than the pushing force exertable by the motor and less than the leak pressure of a stopper seal.

In some embodiments, the housing 1104 can include an additional opening in its sidewall (not illustrated) and a gas permeable membrane can extend across the opening. In such embodiments, the slave cylinder can further include a septum between the gas permeable membrane and the flow path to the reservoir (e.g., through second opening 1114). The trigger assembly can include a needle extending from the end of the piston 1108 through the septum. Sterilant (such as ethylene oxide) can enter the housing 1104 through the membrane and cross the septum through the needle lumen. The needle can have an opening in its sidewall disposed at a location along the needle that remains on the piston side of the septum. As such, sterilant entering through the membrane can pass through the septum, into the housing lumen via the opening in the needle, and into the reservoir 336 via the second opening 1114.

In any of the embodiments disclosed herein, the device can be configured to detect the relative positions of different portions of the trigger assembly and/or cannula carrier to determine an insertion state of the device. For example, for the trigger assembly shown in FIGS. 11A-12B, the relative positions of the pin 1106 and piston 1108 can be measured. In some embodiments, the pin 1106 includes a magnet (not shown) and the portion of the piston 1108 distal of the channel 1110 also includes a magnet (not shown). The magnet on the pin 1106 can be oriented such that, in a pre-insertion position, the north pole of the pin magnet is closest to the piston 1108, and the north pole of the piston magnet is closest to the pin 1106. The durable assembly 200 (or another portion of the infusion device) can include a magnetoresistive sensor that is configured to detect a change in the proximity of the north poles of the pin and piston magnets. Proximity detection of the pin 1106 relative to the piston 1108 (or vice versa) can be beneficial for detecting insertion and for distinguishing cannula insertion from a pre-insertion state. Moreover, because the infusion device can detect insertion, the infusion device can resume basal delivery automatically (if a basal rate was previously set). The relative positions of the pin 1106 and piston 1108 can also initiate plunger seek (in addition to or instead of when the force peaks at the motor).

For many of the components described above in FIGS. 1A-12B, rotational movement is described in a certain direction (e.g., either clockwise or counterclockwise). It will be appreciated that the component and/or device can also be configured to perform its intended function by moving in the opposite direction. For example, the worm gear is described below as rotating counterclockwise to push the plunger pusher forward and clockwise to reverse the plunger pusher. In some embodiments, the worm gear may be configured to rotate clockwise to push the plunger pusher forward and counterclockwise to reverse the plunger pusher. As another example, the cannula carrier is often described as rotating counterclockwise to release the carrier tabs 413. In some embodiments, however, the cannula carrier may be configured to rotate clockwise to release the carrier tabs 413. The motor and/or drive assembly, cannula carrier, ratchet wheel, lever, and/or any component that rotates may similarly have embodiments in which a direction of rotation to achieve a desired outcome is opposite of what is described above.

Conclusion

Although the devices and methods are described in the context of automatic cannula insertion and patch pumps, it should be appreciated that the techniques are equally applicable to a variety of medical devices (e.g., infusion ports) and to a variety of at least partially implantable devices (e.g., sensors). It should also be noted here that the specification describes structures and methods that are especially well-suited for the subcutaneous delivery of high concentration insulin (i.e., U-200 insulin and above) such as U-500 insulin as well as lower concentration insulin such as U-100 insulin. Nevertheless, it should be appreciated that the present inventions are applicable to a wide variety of infusion pumps and medicaments. For example, the present inventions are also applicable to medicaments such as, for example, drugs to mask pain, chemotherapy and other cancer related drugs, antibiotics, hormones, GLP-1, glucagon, various other drugs that include large molecules and proteins that may require a high level of delivery accuracy, as well as to relatively high concentration insulin (i.e., U-200 insulin and above) such as U-500 insulin, as well as lower concentration insulin, such as U-100 insulin.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An infusion device for delivering a medicament to a body of a user, the device comprising:
   an insertion assembly comprising a cannula carrier and a cannula fixed to the cannula carrier, wherein the cannula carrier is configured to rotate from a first position in which the cannula carrier is locked in a pre-insertion state to a second position in which the cannula carrier is free to move to insert the cannula;
   a reservoir assembly comprising a reservoir configured to receive a medicament; and
   a motor configured to rotate in a first direction to cause the medicament to flow out of the reservoir to the cannula, and in a second, reverse direction to cause rotation of the cannula carrier to trigger insertion of the cannula into the user in response to a command from a remote computing device communicatively coupled to the infusion device.

2. The infusion device of claim 1, wherein the cannula carrier is rotationally biased towards the second position.

3. The infusion device of claim 1, further comprising a trigger assembly moveable between a first configuration in which the trigger assembly opposes motion by the cannula carrier towards the second position, and a second configuration in which the trigger assembly allows motion of the cannula carrier towards the second position.

4. The infusion device of claim 3, wherein movement of the motor in the second, reverse direction causes the trigger assembly to move from the first configuration to the second configuration, thereby permitting movement of the cannula carrier for cannula insertion.

5. The infusion device of claim 3, wherein the trigger assembly comprises a ratchet that permits movement of the cannula carrier when the motor rotates in the second, reverse direction.

6. The infusion device of claim 1, further comprising a trigger assembly configured to move out of engagement with the cannula carrier when the motor rotates in the second, reverse direction.

7. The infusion device of claim 1, further comprising a trigger assembly configured to push the cannula carrier into the second position when the motor rotates in the second, reverse direction.

8. The infusion device of claim 1, further comprising a trigger assembly configured to pull the cannula carrier into the second position when the motor rotates in the second, reverse direction.

9. A method for operating an infusion device, the infusion device comprising a reservoir and a plun pusher movable within the reservoir, the method comprising:
moving the plunger pusher in a dispensing direction within the reservoir by rotating a motor of the infusion device in a first direction;
determining a volume of medicament in the reservoir of the infusion device based on the movement of the plunger pusher in the dispensing direction;
receiving a command from a remote controller to rotate the motor in a second direction opposite the first direction; and
rotating the motor in the second direction, thereby causing the infusion device to drive a cannula out of the infusion device.

10. The method of claim 9, further comprising rotating the motor in the first direction, after rotating the motor in the second direction, to deliver the medicament through the cannula.

11. The method of claim 9, wherein:
the infusion device comprises a cannula carrier and the cannula is fixed to the cannula carrier, and
the cannula carrier is configured to rotate from a first position in which the cannula carrier is locked in a pre-insertion state to a second position in which the cannula carrier is free to move to insert the cannula.

12. The method of claim 11, wherein rotation of the motor in the second direction causes the cannula carrier to move from the first position to the second position.

13. The method of claim 11, wherein rotation of the motor in the second direction causes a trigger assembly to push the cannula carrier from the first position into the second position.

14. The method of claim 11, wherein rotation of the motor in the second direction causes a trigger assembly to pull the cannula carrier from the first position into the second position.

15. The method of claim 11, wherein the cannula carrier is biased towards rotating towards the second position.

16. The method of claim 15, wherein rotation of the motor in the second direction causes disengagement of a trigger assembly with the cannula carrier, thereby allowing the cannula carrier to rotate into the second position.

17. The method of claim 9, wherein rotating the motor in the second direction causes simultaneous rotation of a ratchet wheel in the second direction.

18. The method of claim 9, wherein rotating the motor in the second direction activates a linear clutch coupled to a reservoir assembly of the infusion device.

19. A method for operating an infusion device, the method comprising:
receiving a command from a remote computing device to rotate a motor of the infusion device in a first direction, wherein the infusion device comprises an insertion assembly comprising a cannula carrier and a cannula fixed to the cannula carrier:
rotating the motor in the first direction, thereby causing the cannula carrier to rotate from a first, pre-insertion position to a second position in which the cannula carrier is free tomove to insert the cannula;
once the cannula carrier is in the second position, driving the cannula out of the infusion device; and
after rotating the motor in the first direction, rotating the motor in a second direction opposite the first direction to push a medicament stored in a reservoir of the infusion device through the cannula.

* * * * *